US011737876B2

(12) United States Patent
Anderson et al.

(10) Patent No.: US 11,737,876 B2
(45) Date of Patent: Aug. 29, 2023

(54) SYSTEM, DEVICE AND METHOD FOR RESHAPING A VALVE ANNULUS

(71) Applicant: Boston Scientific Scimed, Inc., Maple Grove, MN (US)

(72) Inventors: James M. Anderson, Corcoran, MN (US); John M. Edgell, Plymouth, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 566 days.

(21) Appl. No.: 16/891,378

(22) Filed: Jun. 3, 2020

(65) Prior Publication Data

US 2020/0383783 A1 Dec. 10, 2020

Related U.S. Application Data

(60) Provisional application No. 62/858,547, filed on Jun. 7, 2019.

(51) Int. Cl.
*A61F 2/24* (2006.01)
(52) U.S. Cl.
CPC .......... *A61F 2/2466* (2013.01); *A61F 2/2445* (2013.01); *A61F 2220/0016* (2013.01);
(Continued)

(58) Field of Classification Search
CPC .................. A61F 2/2445; A61F 2/2466; A61F 2220/0016; A61F 2220/0025; A61F 2230/0091
See application file for complete search history.

(56) References Cited

U.S. PATENT DOCUMENTS 9,180,005 B1 * 11/2015 Lashinski ............. A61F 2/2463
9,198,757 B2 12/2015 Schroeder et al.
(Continued)

FOREIGN PATENT DOCUMENTS

WO      0200099 A2    1/2002
WO   2018142275 A1    8/2018

OTHER PUBLICATIONS

International Search Report and Written Opinion for Patent Application No. PCT/US2020/035843, dated Sep. 7, 2020, 14 pages.
(Continued)

*Primary Examiner* — William H Matthews
(74) *Attorney, Agent, or Firm* — Seager, Tufte & Wickhem, LLP

(57) ABSTRACT

A valve annulus repair system joins anchors at one or both of their proximal and distal ends to construct an implant to reshape the annulus. A removable frame may be used to position the anchors proximate to the annulus and to adjust the shape of the annulus. The frame may support the anchors during deployment of the system, release the anchors during construction of the implant, adjust the shape of the implant (and concomitantly the shape of the reconstructed valve) during an adjustment/cinching process, retain the adjusted shape of the valve annulus while relative anchor positions are secured, and release the anchors to enable the frame to be removed from the deployment site following implant construction. With such a system, a low-profile, flexile annular valve implant with reduced the risks of migration, fracture, embolism and thrombus may be provided.

20 Claims, 14 Drawing Sheets

(52) U.S. Cl.
CPC .............. *A61F 2220/0025* (2013.01); *A61F 2230/0091* (2013.01); *A61F 2250/001* (2013.01)

(56) References Cited

U.S. PATENT DOCUMENTS

| | | | |
|---|---|---|---|
| 9,610,156 | B2 | 4/2017 | Lashinski |
| 10,335,275 | B2 | 7/2019 | Lashinski et al. |
| 10,555,813 | B2 | 2/2020 | Lashinski et al. |
| 2003/0074012 | A1 | 4/2003 | Nguyen et al. |
| 2010/0217283 | A1 | 8/2010 | St. Goar et al. |
| 2011/0082538 | A1 | 4/2011 | Dahlgren et al. |
| 2017/0135816 | A1* | 5/2017 | Lashinski ............. A61F 2/2445 |
| 2018/0064535 | A1 | 3/2018 | Gilmore et al. |
| 2018/0368830 | A1 | 12/2018 | OCarroll et al. |
| 2019/0053903 | A1 | 2/2019 | Rohl et al. |
| 2019/0142591 | A1 | 5/2019 | Rohl et al. |
| 2019/0159770 | A1 | 5/2019 | Rohl et al. |
| 2019/0336288 | A1* | 11/2019 | Gross .................... A61F 2/2445 |
| 2020/0022811 | A1* | 1/2020 | Griswold ............. A61F 2/2439 |
| 2020/0121461 | A1* | 4/2020 | Bruner ................. A61F 2/2445 |

OTHER PUBLICATIONS

Cardioband Mitral Reconstruction System key advantages, Cardioband Mitral System|Edwards Lifesciences; https://www.edwards.com/gb/devices/transcatheter-valve-repair/cardiobandmitralsystem © 2018 Edwards Lifesciences Corporation.

Edwards Cardioband Mitral Reconstruction System. Introduction and overview, Two-year follow up on CE trial. Edwards Lifesciences (39 slides). © 2018 Edwards Lifesciences Corporation.

* cited by examiner

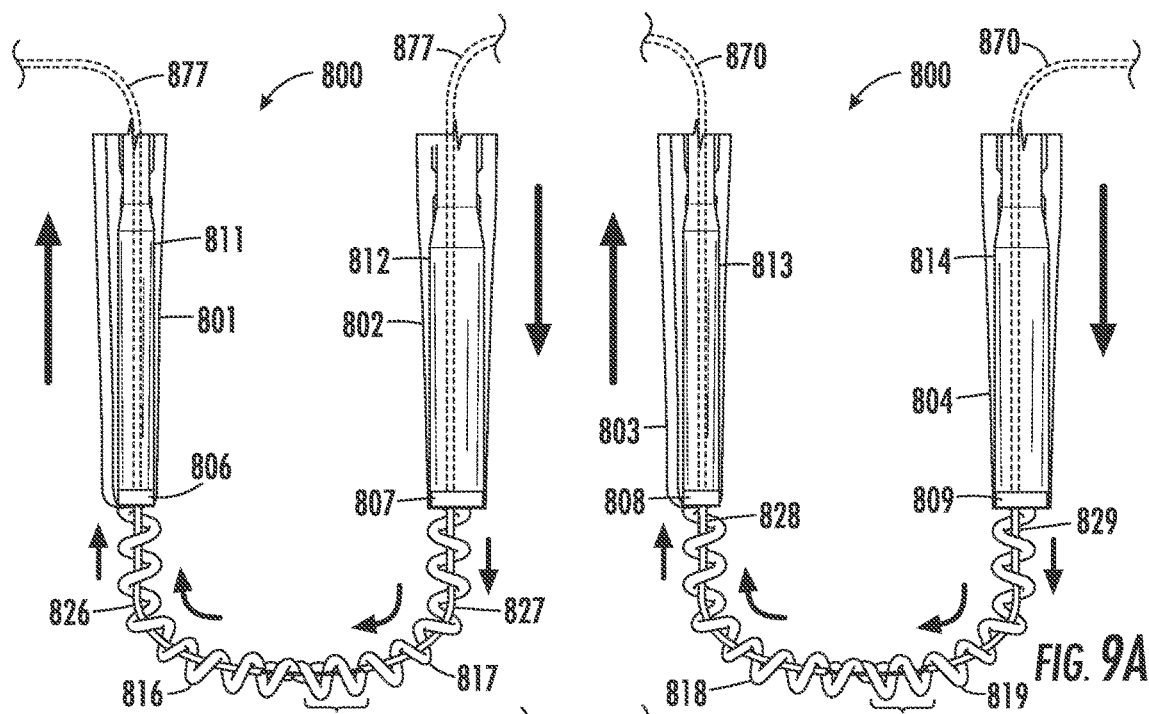
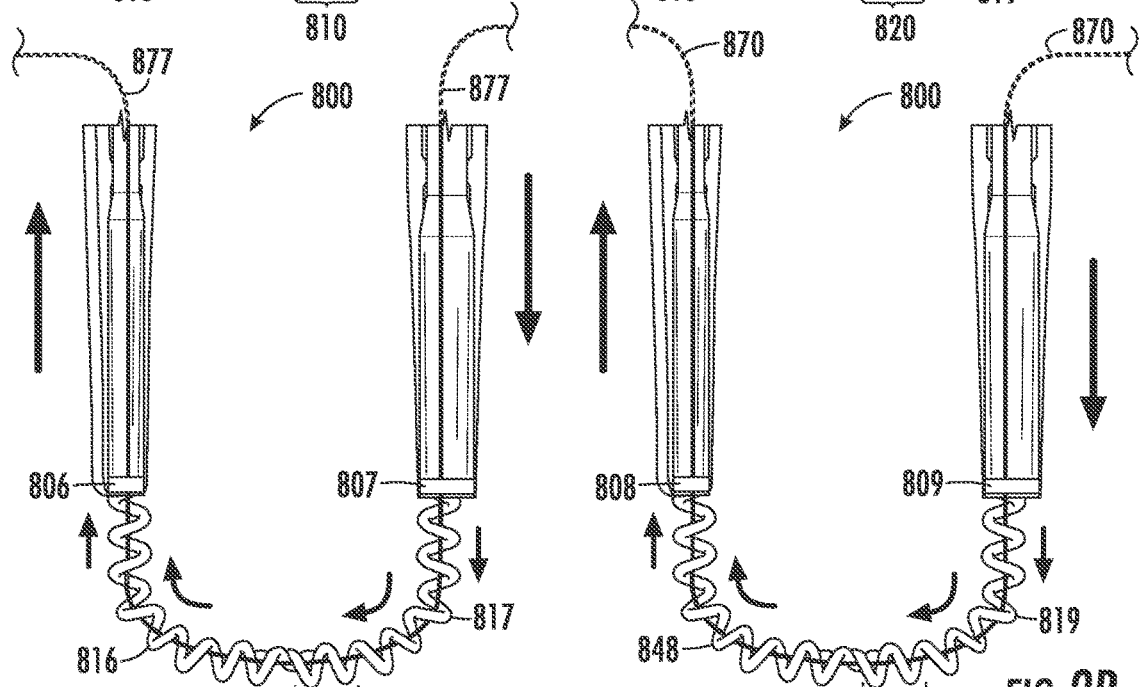
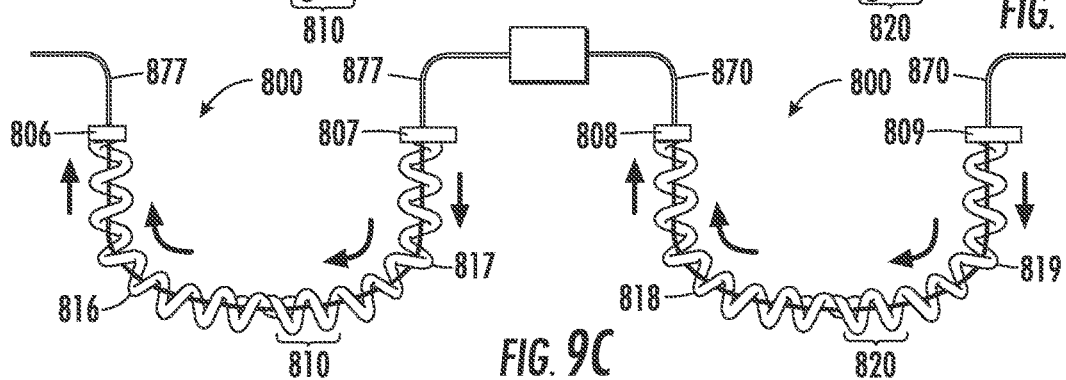

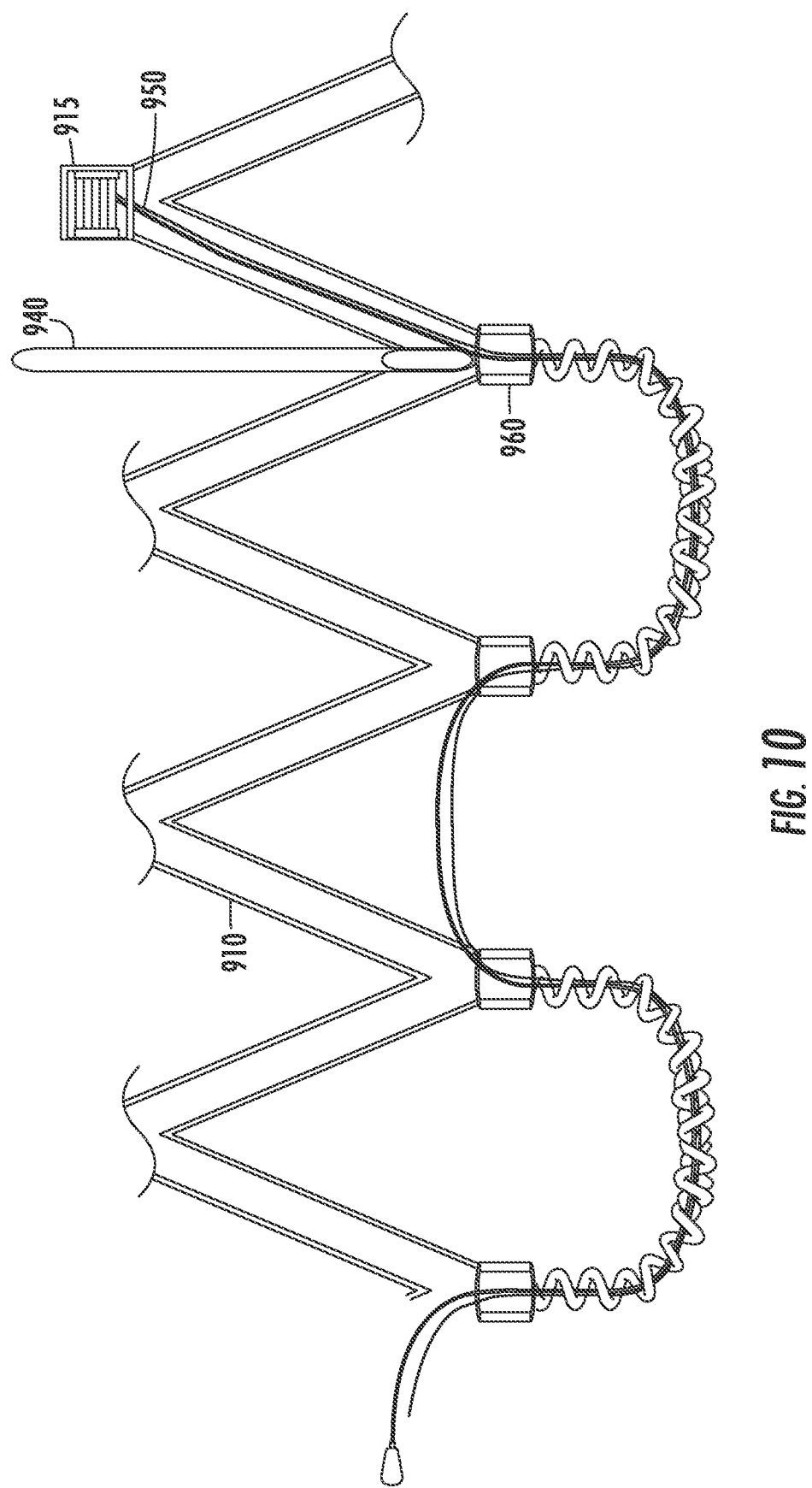

SYSTEM, DEVICE AND METHOD FOR RESHAPING A VALVE ANNULUS

CROSS-REFERENCE TO RELATED APPLICATIONS

The present application claims the benefit of priority under 35 U.S.C. § 119 to U.S. Provisional Patent Application 62/858,547, filed Jun. 7, 2019, which application is incorporated herein by reference in its entirety for all purposes.

FIELD

The present disclosure relates generally to the field of implantable medical devices and more particularly to implantable devices, systems, and methods for reconfiguring heart features.

BACKGROUND

The mitral valve lies between the left atrium and the left ventricle of the heart. The mitral valve is comprised of two leaflets, an anterior leaflet, and a posterior leaflet, which coapt during systolic contraction. The opening of the mitral valve is surrounded by the mitral annulus comprised of a fibrous ring that supports the valve's leaflets. In a healthy heart, blood flows through an open mitral valve during diastole with contraction of the left atrium, and mitral valve leaflets close during systole with contraction of the left ventricle.

Mitral insufficiency (MI) (also referred to as mitral regurgitation or mitral incompetence) is a form of heart disease where the mitral annulus dilates excessively and the valve leaflets no longer effectively close, or coapt, during systolic contraction. Consequently, regurgitation of blood occurs during ventricular contraction and cardiac output decreases.

The goal of mitral valve annuloplasty is to regain mitral valve competence by restoring the physiological form and function of the normal mitral valve apparatus, including one or more of the mitral valves and the mitral annulus. One method of mitral valve annuloplasty includes surgical implantation of an annuloplasty ring. During the operation, a surgeon positions the annuloplasty ring proximate the valve annulus and sutures it in place to thereby restore the valve annulus approximately to its native configuration. Annuloplasty ring placement is an invasive and time-consuming procedure that poses risks of morbidity and mortality due to stroke, thrombosis, heart attack and extended recovery time.

Some transluminal mitral valve annuloplasty techniques use a deployment catheter and transluminal navigation to deliver a reconstructive implant to a mitral valve treatment site. In such systems an implant may be compressible to a first, reduced diameter for transluminal navigation and deployment to the left atrium of a heart. The implant may then expand to a second, enlarged diameter to embed its anchors to the tissue surrounding and/or including the mitral valve. The implant may then contract to a third, intermediate diameter, pulling the tissue radially inwardly, thereby reducing the mitral valve and lessening any of the associated symptoms including mitral regurgitation.

Whether through surgical or transluminal delivery, current valve annulus implants may tend to be subject to problems associated with migration and/or device fracture. In addition, implant size may cause the implant to project into the atrium, undesirably contacting patient tissue and subjecting the patient to embolic risk and/or thrombus over time. It is with these considerations in the mind that the improvements of the present disclosure may be useful.

SUMMARY

Embodiments of the present disclosure relate to a system, device, and method for reshaping a valve annulus such as a heart valve annulus. According to one aspect, a system comprises a catheter comprising a plurality of lumens extending from a proximal end of the catheter to a distal end of the catheter. The system includes a frame having a compressed configuration enabling translational advancement of the frame through the catheter, the frame comprising a first configuration enabling positioning of the frame at least partially around a valve annulus and at least one cinch mechanism coupled to the frame and configured to transition the frame between the first configuration and a second configuration different from the first configuration. A plurality of anchors may be supported by the frame, each anchor comprising a proximal end comprising an anchor head and a distal end configured for mated engagement with another anchor of the plurality of anchors to form a conjoined anchor pair, each anchor comprising an anchor lumen extending from a proximate anchor end to a distal anchor end. The system includes a guidance device that is axially translatable within the anchor lumen and through tissue of the valve annulus, the guidance device configured to define a path through tissue of the valve annulus from a first anchor towards a second anchor, the first anchor translatable over the guidance device along the path through the tissue of the valve annulus towards the second anchor to form a conjoined anchor pair.

In various embodiments, the first configuration comprises a tissue engaging configuration and the second configuration comprises an annulus reshaping configuration, and wherein the first configuration is larger than the second configuration. A binding mechanism may be provided to secure the plurality of anchors in positions associated with the annulus reshaping configuration to retain the annulus reshaping configuration. The binding mechanism may comprise one or more of a cinch wire, a suture wire or an anchor clip and one or more of a cinch clamp or a resistance weld band.

The system may include a plurality of drive tubes, each drive tube disposed within one of the plurality of lumens of the catheter, one drive tube coupled to each anchor, wherein each drive tube is configured to advance an associated anchor over the guidance device. The guidance device may be configured for axial translation through a drive tube lumen of a drive tube into the anchor lumen. The guidance device in some embodiments may comprise a curved distal end configured to direct the anchor away from a plane normal to the valve annulus. In various embodiments, the drive tube may be configured to translate the distal anchor end past the curved distal end of the guidance device. In some embodiments, the guidance device comprises at least one of a guide-wire or a guide tube. In some embodiments the guidance device may comprise a guide tube and wherein the binding mechanism couples paired anchor heads through a lumen of the conjoined anchor pair.

In various embodiments, the frame may comprise a plurality of anchor sleeves corresponding in number to the plurality of anchors, each anchor sleeve configured to releasably support an associated anchor for deployment of the associated anchor at least partially around a valve annulus. The cinch mechanism may comprise a cinch wire surrounding one of an internal or external radius of the frame, and a drive tube configured to withdraw the cinch wire to reduce an internal volume of the frame. In some embodiments, the frame may comprise a plurality of upper crowns, each upper crown comprising a pair of struts having a space therebetween, and the cinching mechanism comprises a plurality of collars, each collar at least partially surrounding each upper crown and configured to translate axially relative to the frame to adjust the space between the pair of struts of an associated upper crown. In some embodiments, the plurality of anchors may comprise a plurality of helical coils, and wherein the conjoined anchor pair comprises a plurality of overlapping coils of a helical coil pair.

According to a further aspect, an implant includes a plurality of anchors, each anchor comprising a distal end sharpened for advancement through tissue of a valve annulus towards another of the plurality of anchors, each anchor configured for mating engagement with the another of the plurality of anchors when embedded in the tissue of the valve annulus to form a conjoined anchor pair, and a binding mechanism, coupling proximal ends of at least two anchors, to retain the at least two anchors in a predetermined configuration.

According to some embodiments, the predetermined configuration is a valve annulus reshaping configuration and the binding mechanism comprises one or more of a cord, a wire, a filament and a clip. Each anchor may comprise a proximal end comprising an anchor head and wherein the binding mechanism couples together at least some of the anchor heads of the plurality of anchors. The conjoined anchor pair may include an anchor lumen extending at least partially therethrough and the binding mechanism may couple a pair of anchor heads using a path including the anchor lumen.

According to another aspect, a method for reshaping a valve annulus includes the steps of deploying an expandable frame releasably supporting a plurality of anchors through a delivery catheter to a valve annulus repair site. The method may include driving at least two of the plurality of anchors into tissue around the valve annulus including matingly engaging distal tips of anchors to form an anchor pair at least partially around the valve annulus and compressing the expandable frame to reshape the valve annulus to an annular reshaping configuration. The method may include binding proximal ends of anchor pairs, releasing the plurality of anchors from the expandable frame and removing at least a portion of the expandable frame from the valve annulus repair site.

According to various embodiments, the step of driving the plurality of anchors into tissue around the valve annulus includes the steps of, for each pair of anchors of the plurality of anchors, selecting an anchor including identifying a paired anchor, inserting a guidance device through a first lumen extending from a proximal end of the delivery catheter through a distal anchor tip of the selected anchor, wherein the guidance device comprises a curve at a distal tip configured to guide the selected anchor to the paired anchor and wherein inserting the guidance device through the distal anchor tip of the selected anchor cuts a first path through tissue towards the paired anchor, advancing the selected anchor over the guidance device towards the anchor pair, inserting a guidance device through a second lumen extending from a proximal end of the catheter through a distal anchor tip of the paired anchor, wherein the curve at a distal tip of the guidance device cuts a path through tissue towards the selected anchor, advancing one or both of the selected anchor and the paired anchor towards each other to conjoin distal ends of the selected anchor and the paired anchor.

With such an arrangement, a low-profile valve annulus implant with increased flexibility and reduced potential for migration, fracture, thrombus and embolic risk is provided.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 9A, 9B, and 9C illustrates several steps of a binding system and method in accordance with an embodiment of the present disclosure;

FIG. 10 is a diagram illustrating a device and method enabling coupling of proximate anchor ends using a single cinch cord for multiple anchor pairs in accordance with an embodiment of the present disclosure;

DETAILED DESCRIPTION

Figure 1:
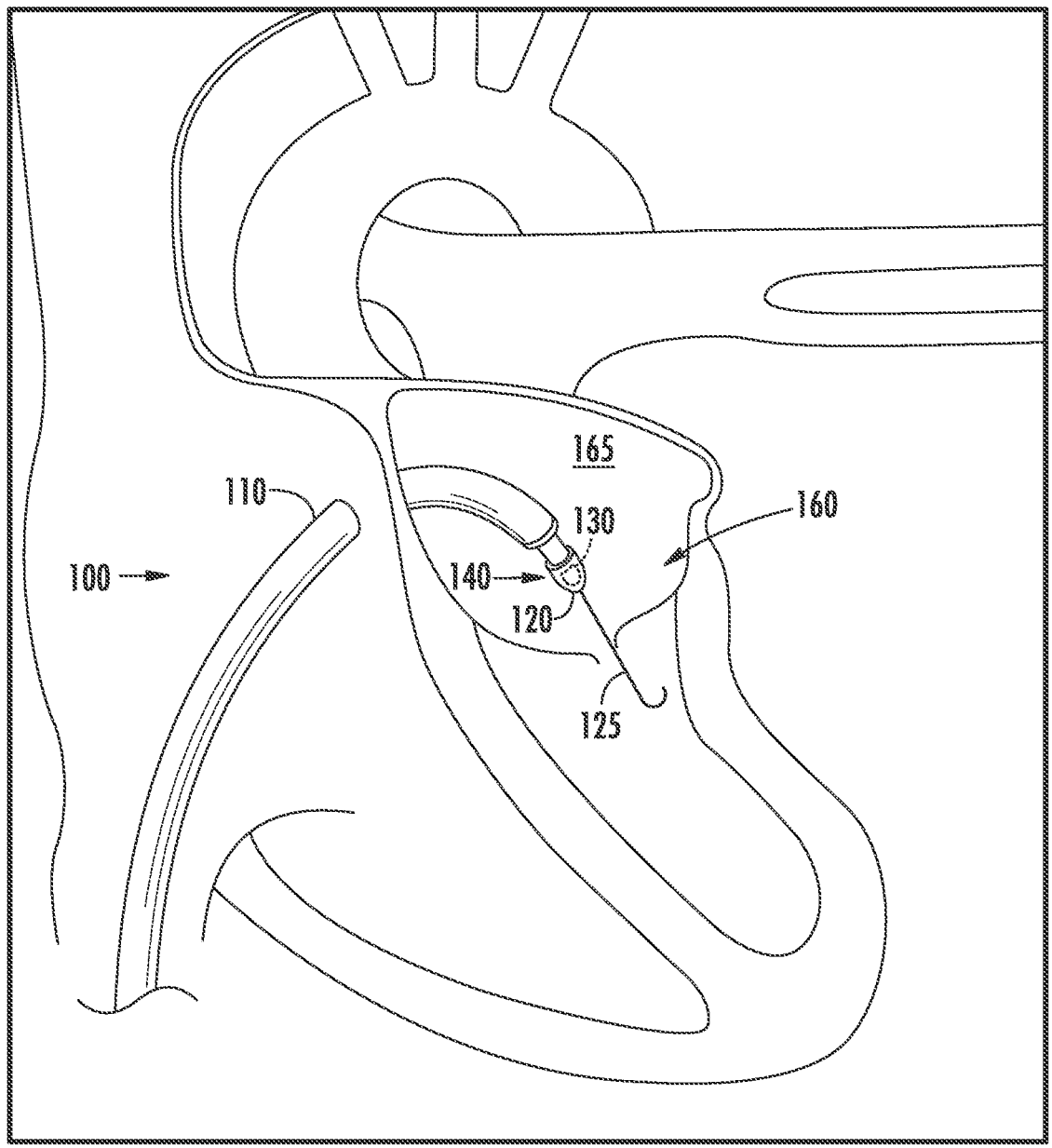
FIG. 1 is diagram illustrating an implant deployment system in accordance with an embodiment of the present disclosure.

According to one aspect, an improved valve annulus reshaping system enables construction of a valve annulus implant proximate to a valve annulus through deployment and conjoining of implant anchors. The anchors may advantageously be configured to conjoin at one or both of their proximal and distal ends to construct the implant. In one embodiment, positioning of the anchors proximate to the valve may be facilitated using a removable frame or other structure. The frame may be configured to support the anchors during deployment of the system, release of the anchors for construction of the implant, adjust the shape of the implant (and concomitantly the shape of the reconstructed valve) during an adjustment/cinching process, retain the adjusted shape of the valve annulus while securing relative anchor positions, and release the anchors for frame removal from the deployment site.

With such a system, a low-profile valve annulus implant with increased flexibility is provided with several advantages over the prior art. The constructed implant's conjoined anchor design provides a low-profile solution that minimizes implant bulk and the related potential for implant fracture and/or contact between the heart tissue and the implant, thereby reducing embolic and thrombus risk. An angularly embedded and conjoined anchor architecture provides structural integrity and improved implant retention over prior art methods that drive anchors relatively straight down into tissue. As a result, the forces required to displace the implant greatly increase in strength and complexity, thereby reducing the potential for implant migration. In addition, the conjoined anchor structure moves more flexibly with the patient's anatomy, reducing trauma over time.

These and other beneficial aspects of an embedded implant and method of deployment are described in more detail below. It should be noted that, although embodiments of the present disclosure may be described with specific reference to mitral valves, the principles disclosed herein may be readily adapted to facilitate reconstruction of any valve annulus, for example including a tricuspid valve annulus and/or may similarly benefit any other dilatation, valve incompetency, valve leakage and other similar heart failure conditions.

As used herein, the singular forms "a," "an," and "the" are intended to include the plural forms as well, unless the context clearly indicates otherwise. The terms "comprises" and/or "comprising," or "includes" and/or "including" when used herein, specify the presence of stated features, regions, steps, elements, and/or components, but do not preclude the presence or addition of one or more other features, regions, integers, steps, operations, elements, components, and/or groups thereof.

As used herein, the term "distal" refers to the end farthest away from the medical professional when introducing a medical device into a patient, while the term "proximal" refers to the end closest to the medical professional when introducing a medical device into a patient.

As used herein, the conjunction "and" includes each of the structures, components, features, or the like, which are so conjoined, unless the context clearly indicates otherwise, and the conjunction "or" includes one or the others of the structures, components, features, or the like, which are so conjoined, singly and in any combination and number, unless the context clearly indicates otherwise.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

Referring now to FIG. 1, an exemplary valve annulus reshaping system 100 includes a deployment catheter 110 having a distal tip 120 comprising a distal sheath 140 and an extendable guidewire 125 extending therethrough to guide the deployment catheter 110 into position proximate to a valve annulus 160. Guide wire 125 may measure, for example, between 0.010 inches and 0.038 inches in diameter. Deployment catheter 110 may measure about twenty to thirty centimeters in length for accessing the mitral valve through the apex of the heart. Deployment catheter may access the vasculature of the leg, in particular the femoral vein or the iliac vein for transluminal deployment to a cardiac annulus.

In one embodiment, components of a conjoined anchor implant deployment system 130 are disposed within the distal sheath 140 of the deployment catheter during deployment. In FIG. 1 the distal end of the deployment catheter 110 is maneuvered into the left atrium 165 to a position above and/or around and/or partially around the mitral valve annulus 160. According to one aspect, the deployment catheter may have various positioning and imaging capabilities, for example such as those described in U.S. patent Ser. No. 15/280,004 entitled "Methods for Deployment of Heart Valve Devices Using Intravascular Ultrasound Imaging", filed Sep. 29, 2016, incorporated herein by reference.

Figure 2:
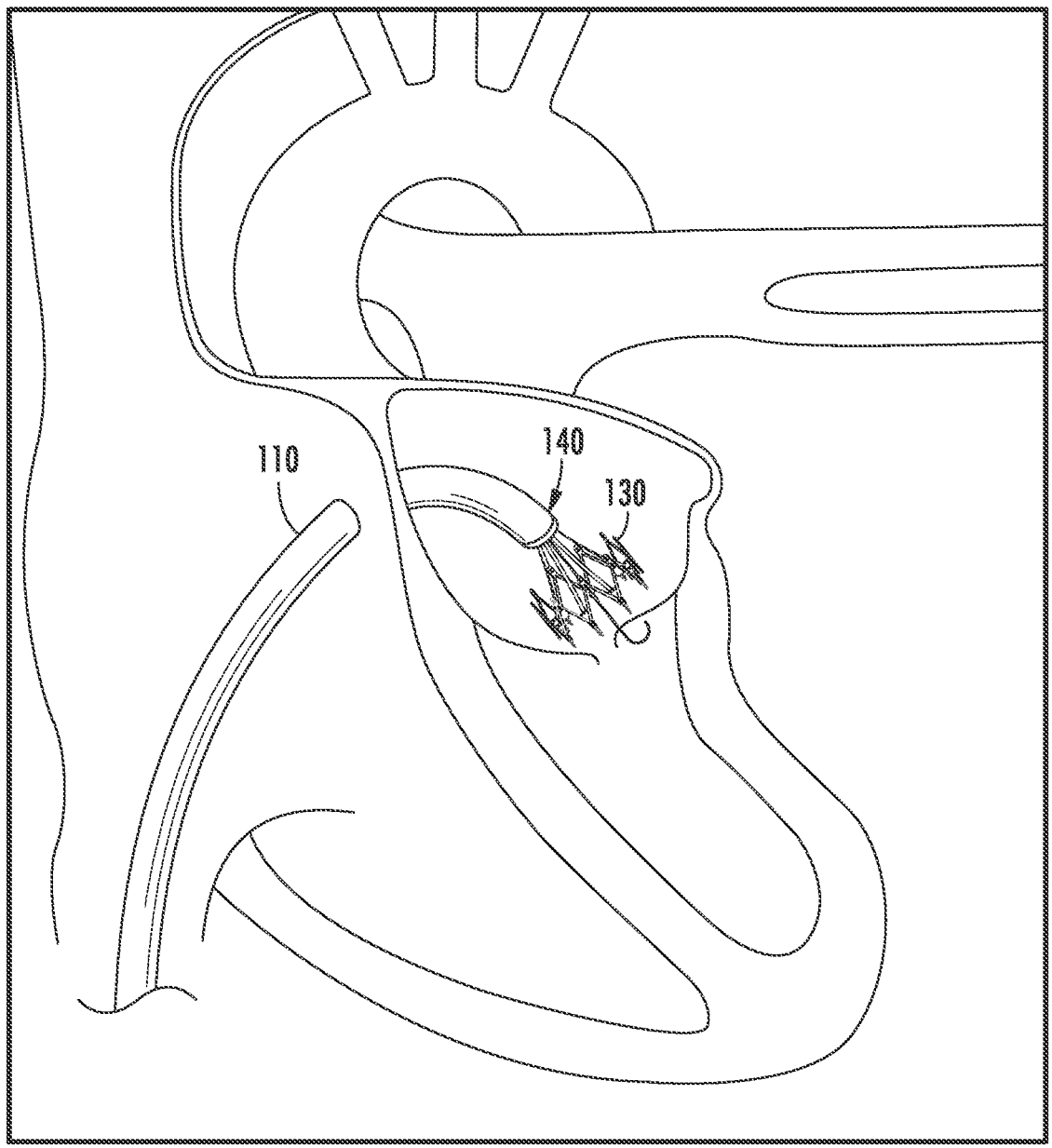
FIG. 2 illustrates an expanded frame in accordance an embodiment of the present disclosure.

Referring now to FIG. 2, when the distal tip of the deployment catheter 110 is appropriately positioned, the components of implant 130 may be exposed (either by advancing the implant 130 through distal sheath 140 or by withdrawing the distal sheath 140 over the implant) and expanded to a working diameter. Expansion may occur naturally, for example when the frame is formed of Nitinol or other shape memory or super elastic materials that is biased towards an expanded state. In alternate embodiments, expansion may be mechanically controlled, for example through the use of a force applied within the frame using an inflatable balloon or the like. The systems and method disclosed herein are not limited to any particular mechanism for positioning anchors for annular reconstruction, whether such positioning uses a ring or an expandable frame, and for example may use techniques described in U.S. Pat. No. 9,610,156 "Mitral Valve Inversion Prostheses" filed Dec. 24, 2014, U.S. Pat. No. 9,180,005 "Adjustable Endoluminal Mitral Valve Ring", filed Nov. 24, 2015 and U.S. patent application Ser. No. 15/352,288, entitled "Implantable Device And Deployment System For Reshaping a Heart Valve Annulus" filed Nov. 16, 2016, each incorporated by reference herein.

Figure 3A:
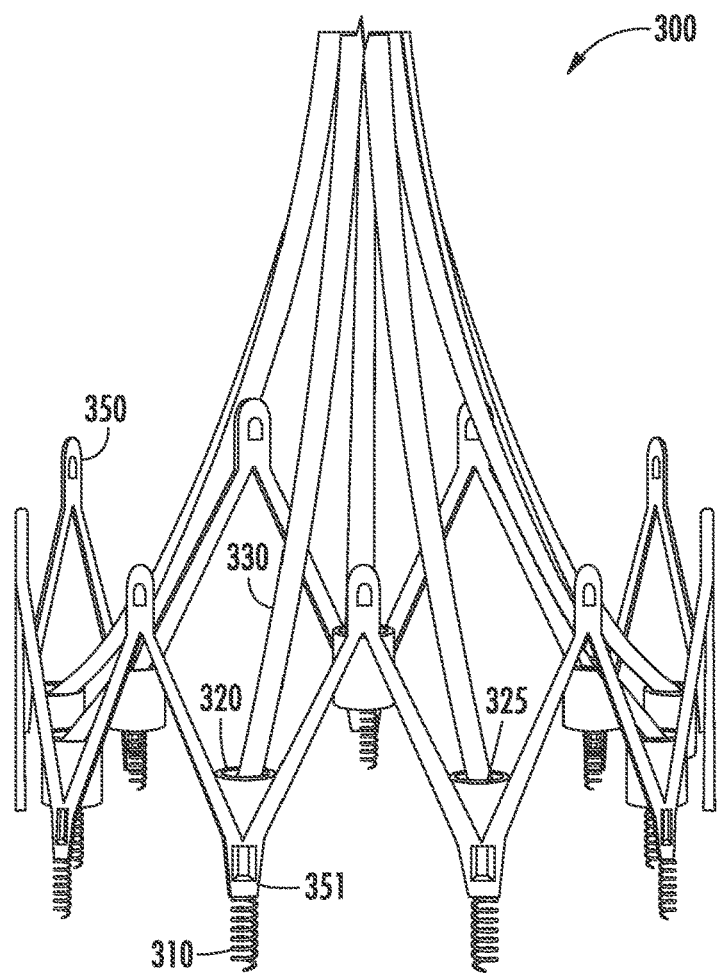
FIGS. 3A-3C illustrate aspects of the frame of FIG. 2 in more detail.
Figure 3B:
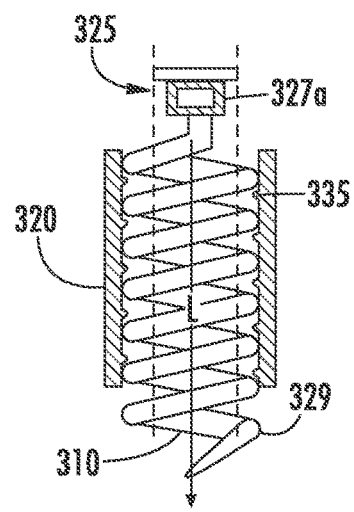
Figure 3C:
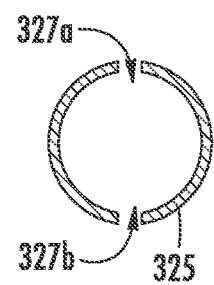

FIGS. 3A-3C illustrate exemplary components that may be included in an embedded implant deployment system 300 disclosed herein. The components of the deployment system 300 may include a frame 350 comprising one or more anchor sleeves 320, each anchor sleeve for releasably supporting an anchor 310. Each anchor 310 may include an anchor head 325 configured to engage with a drive tube 330 to enable the drive tube to advance the anchor through the frame 350 as described in more detail below.

Frame 350 may be constructed from, for example, metallic materials and/or polymers with sufficient structural integrity to reshape a mitral valve. The material may also be chosen based on biocompatibility and fatigue resistance. Frame material(s) could include stainless steel, Nickel-Titanium, Cobalt-Chromium, Pyrolytic Carbon, Nitinol, polymer materials (e.g., PEEK), and/or other suitable frame materials. In some cases, the frame may also be coated with drug-eluting material to prevent fibrosis and/or clotting.

The frame 350 may be laser cut from a tubular member to form the basic shape. The frame may also be heat-set into a shape for further assembly, which may include the further steps of electrochemical etching and/or a secondary polishing to remove irregular and/or unwanted material. These further steps may be used to smoothen the surface of the frame. Alternatively, and as described in more detail below, the frame may be formed of or include a tubular frame structure wherein the lumen defined by the tubular frame may be configured to carry cinch cord and/or suture material for conjoining the proximal anchor heads of anchor pairs.

In the embodiment of FIG. 3A, the frame 350 is shown comprised of a plurality of sinusoidal strut elements joined at proximal and distal apexes to create a zigzag pattern. Anchor sleeves 320 may be positioned at one or more distal apex of the frame 350, where each anchor sleeve 320 is configured to releasably support an anchor.

In various embodiments the anchor sleeve 320 may be configured to secure the anchor 310 during positioning and deployment of the frame 350 and to enable advancement of the anchor through the sleeve and away from the frame during anchor deployment. For example, FIG. 3B illustrates a cross section of an exemplary embodiment of an anchor sleeve 320, shown supporting an anchor 310.

The anchor 310 is shown to include a proximal end comprising an anchor head 325 and a distal end comprising a helical coil having a sharpened distal tip. In various embodiments the anchor 310 may be made of a suitable biocompatible metal alloy such as stainless steel, cobalt chromium, platinum iridium, nickel titanium, other suitable materials, or combinations thereof. Each anchor 310 may be sharpened at its distal point, or leading turn, so as to facilitate penetration into the cardiac tissue. Each anchor 310 may be from about ten to about fifteen millimeters (mm) in total axial length. In some embodiments, the anchors 310 may be shorter or longer than ten to fifteen millimeters (mm) in total axial length. By "total" axial length it is meant the axial length of the anchor 310 from the end of the distal penetrating tip to the opposite, proximal end anchor head 325. The helical portion of the anchor 310 may be from about six to about twelve millimeters (mm) in axial length, i.e. in an axial direction. In some embodiments, the helical portion of the anchor 310 may be shorter or longer than six to twelve millimeters (mm) in axial length. The anchor head and/or other non-helical portions of the anchor 310 may be from about three to about four millimeters (mm) in axial length. In some embodiments, the anchor head 325 and/or other non-helical portions may be shorter or longer than three to four millimeters (mm) in axial length. As described in more detail later herein, according to one aspect the pitch and angle of the helical coils is selected to allow pairs of helical coils to conjoin when the distal ends are rotated for mating engagement. According to one aspect, the helical coil of anchor 310 defines an anchor lumen L 326 (having a diameter indicated by dashed lines in FIG. 3B) that may extend at least partially from the anchor head 325 through the distal turn 329 of anchor 310. In some embodiments, the helical diameter range may extend from (0.050"-0.080"), and pitch from (0.030"-0.080"), such that coil pitch angle is about twenty (20) degrees.

The anchor sleeve 320 may be generally cylindrical in shape and formed from metallic materials and/or polymers with sufficient structural integrity for supporting anchors for driving into the heart annulus. The length of the sleeve may range from between approximately half the length of the coil (~3 mm in some embodiments) to about twice the length of the coil (in the range of 20 mm, for example). The material may also be chosen based on biocompatibility and fatigue resistance. Material(s) could include stainless steel, Nickel-Titanium, Cobalt-Chromium, Pyrolytic Carbon, Nitinol, polymer materials (e.g., PEEK), and/or other suitable frame materials. In some cases, the anchor sleeves may also be coated with drug-eluting material to prevent fibrosis and/or clotting.

Anchor sleeves 320 may be formed within the frame 350 or may be attached or otherwise joined to the frame. Anchor sleeves may be positioned on the frame to orient anchors towards annular tissue when the system is positioned for annular reconstruction. For example, in a transseptal deployment of the implant, the distal apex 351 of the frame 350 contact the valve annulus when the embedded implant components are positioned for annular reconstruction. For transapical deployment, the proximal apex of a frame may surround the annular tissue, and the anchor sleeves may be mounted on or about the proximal apices of the frame to orient the anchors towards the annular tissue.

Anchor sleeve 320 is shown to include internal features, such as groove 335, matched in pitch and angle to the pitch and angle of the anchor 310 such that rotation of the anchor results in translation of the anchor along a longitudinal axis L of the anchor sleeve 320. According to one aspect, the internal diameter of the anchor sleeve is configured to slideably accommodate a drive tube while enabling the groove 335 to support the anchor 310 when it is within the sleeve 320. With such an arrangement, a drive tube coupled to the anchor head may freely advance the anchor 310 away from frame 350, into annular tissue and towards a paired anchor as described below.

According to one aspect, anchor head 325 may be configured for releasable engagement with a drive tube 330. Anchor head 325 may include one or more notches for engaging one or more retractable, hooks, flanges, or extensions within the drive tube 330. Drive tube 330 may comprise a hypo tube or similar device configured to transmit a torque along its length for anchor rotation. A cross section of an exemplary anchor head 325 is shown in FIG. 3C to include a pair of notches 327a, 327b. In one embodiment, extensions in the drive tube may extend into the notches 327a, 327b to enable rotation of the anchor by the drive tube. The extension may subsequently be withdrawn to release the anchor when annuloplasty is completed.

Figure 4:
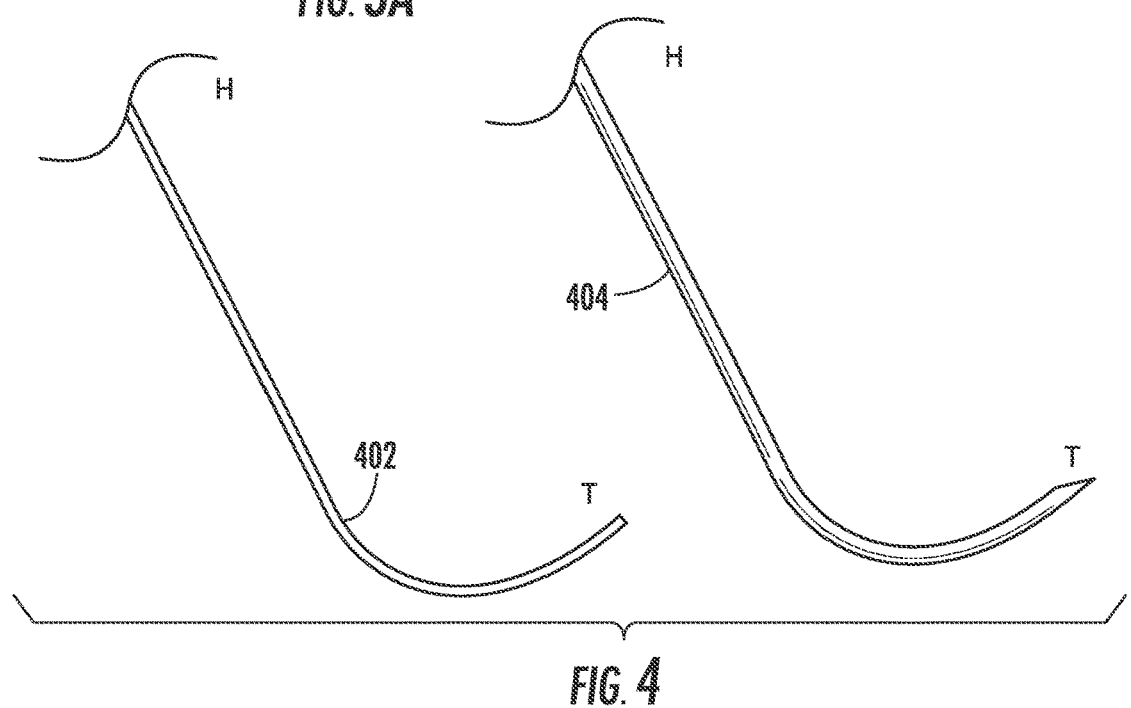
FIG. 4 illustrates respective a guidewire and a guide tubes in accordance with an embodiment of the present disclosure.

Referring now to FIG. 4 according to one aspect the embedded implant deployment system includes a guidance device such as guidewire 402 or guide tube 404. The guidance device is generally curved in shape to provide a displacement between a head H of the guidance device and the tail T of the guidance device of between 45 and 90 degrees. The guidewire may comprise, for example an inner core shaft, an outer coating or sheath and a tip, for example a stainless steel pre-shaped coil covering a monofilament core and painted with a thin layer of Teflon to reduce surface friction.

The guide tube 404 may comprise a pre-shaped cylindrical tube formed of a material chosen based on biocompatibility and fatigue resistance. Material(s) could include stainless steel, Nickel-Titanium, Cobalt-Chromium, Pyrolytic Carbon, Nitinol, polymer materials (e.g., PEEK), and/or other suitable frame materials.

The guidance device(s) 400 may be used during embedded implant construction as will be described with regard to FIGS. 5A-5D.

Figure 5A:
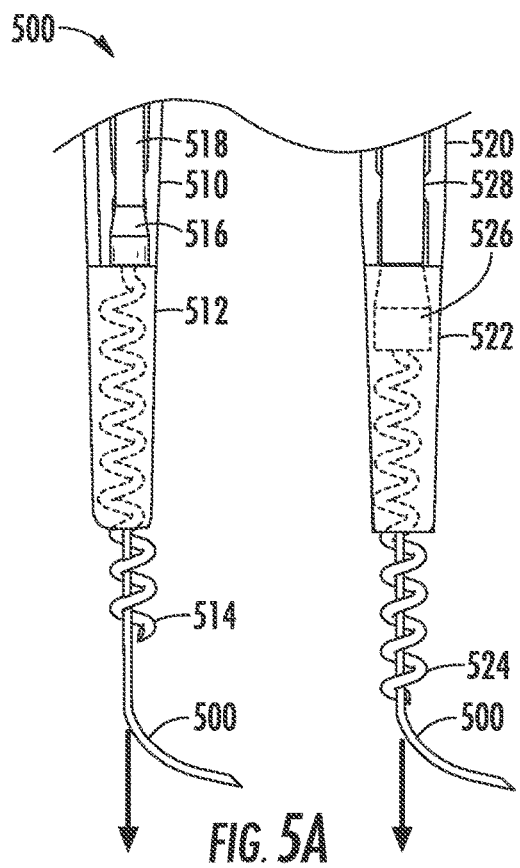
FIGS. 5A-5D illustrate exemplary steps that may be performed to conjoin anchor pairs of the implant in accordance with an embodiment of the present disclosure.

FIG. 5A illustrates a frame portion 500 that may be used in a system described herein, showing a pair of struts 510 and 520. Strut 510 is shown to include an anchor sleeve 512 which may be configured as described with regard to FIG. 3B to support the anchor 514 during deployment to a valve annulus. Strut 520 is similarly shown to include an anchor sleeve 522 for supporting anchor 524 during deployment. Each anchor 514, 524 is shown to include a respective anchor head 516, 526 which couple the associated anchor to a respective drive tube 518, 528. According to one embodiment, the drive tubes comprise rotational drive tubes configured such that rotation of the drive tube distally translates the coupled anchor. In one embodiment, anchors 514, 524 comprise helical coils, each helical coil defines an anchor lumen that extends from the distal tip of the anchor through the respective anchor heads 516, 526.

It should be noted that although helical coil anchors are described, other forms of anchors that comprise one or more features such as sharpened distal tips that enable the anchor to be driven through tissue, features promoting tissue ingrowth for securing the anchor in the tissue, and lumens extending at least partially therethrough for guiding the anchor through the tissue may be substituted interchangeably herein without affecting the scope of the invention.

When the frame portion 500 is positioned at a deployment site proximate to the valve annulus, the process of implant construction, including conjoining of at least some of the distal anchor ends and conjoining of at least some of the proximal anchor ends, begins.

Figure 5B:
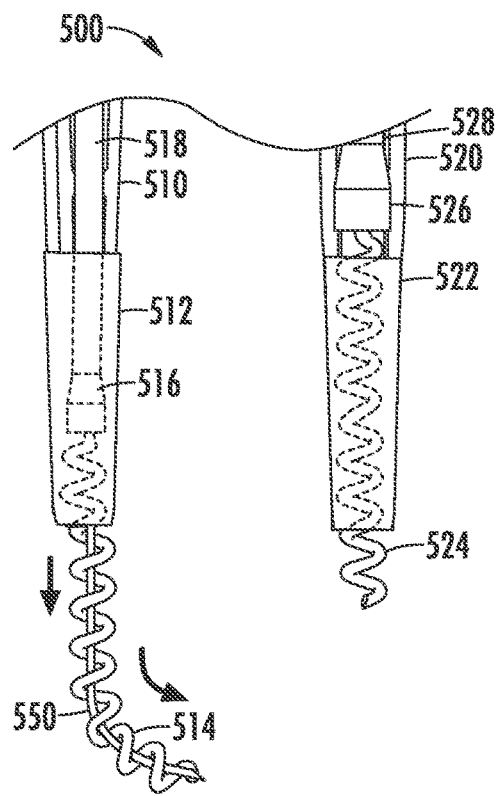
Figure 5C:
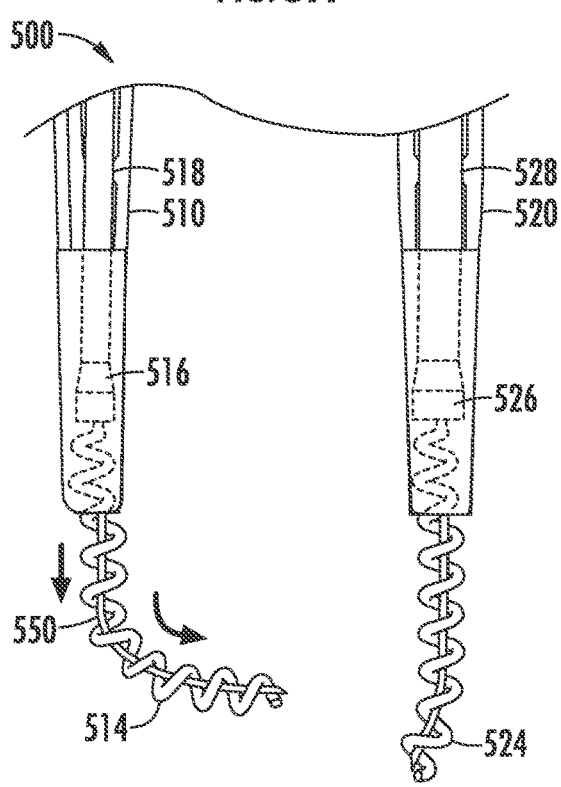
Figure 5D:
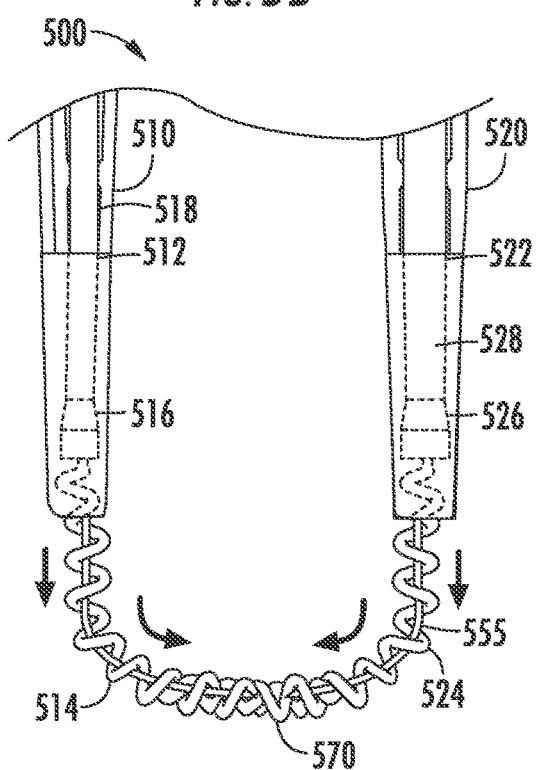

Conjoining at least some of the distal ends of the anchors includes conjoining the distal ends of pairs of adjacent anchors as shown and described in FIGS. 5B-5D. As shown in FIG. 5B, conjoining anchor pairs includes inserting a guidance device 550 through drive tube 518, anchor head 516 and anchor lumen. As described with regard to FIGS. 4A and 4B, the guidance device 550 may comprise a curved guide wire or guide tube. As illustrated in FIG. 5A, a guidance device 550 generally is advanced before the anchor 514, 524 is advanced. In some embodiments the guidance device 550 is a J-shaped wire. The anchor 514, 524 can be partially advanced out of the anchor housing or sleeve 512 up to the bend in the guidance device 550. The bend in the guidance device 550 preferably advances before the following anchor 514, 524 is advanced. The guidance device 550 may be advanced into the annular tissue at a location proximate to anchor sleeve 512. Due to the curved nature of the guidance device 550, as the guidance device 550 is inserted into the tissue, reactive forces divert the distal tip of the guidance device away from the normal plane of the annulus. In one embodiment, the guidance device 550 may be advanced to an intermediate position between a pair of anchors such as anchor 514 and anchor 524. Navigation of the guidance device 550 may be performed using any one of a variety of imaging technologies, including but not limited to an intravascular cardiac echography (ICE) catheter. Drive tube 518 may be activated to translationally advance the anchor 514 over the guidance device 550 to the intermediate position as shown in FIG. 5B. FIG. 5B illustrates anchor 514 advanced to an intermediate position, such that the distal end of the anchor 514 is proximate to the distal end of the guidance device 550.

Once anchor 524 is positioned, referring now to FIG. 5C, the second anchor of the pair (here anchor 524) may be advanced into annular valve tissue. A guidance device 555 may be inserted through drive tube 528, extending through anchor sleeve, 522, anchor head 526, anchor lumen 529 and past the distal tip of anchor 524. In some embodiments, rotation of drive tube 528 translates the anchor through anchor sleeve 522 and towards the distal tip of anchor 514.

As shown in FIG. 5D, once the distal tips of the anchors 514 and 524 are aligned, either of both of drive tube 518 and 528 may continue to drive their respective anchors 514 and 524 towards each other. As the anchors are rotated, the turns of helical anchor 524 join with the turns of helical anchor 514 to form a conjoined anchor lumen 570. Anchors may continue to be rotated relative to each to provide structural integrity to the anchor lumen. In various embodiments, structural integrity may be measured based on factors including the likelihood that one or both of the anchors forming an anchor migrate or are displaced. According to one aspect, structural integrity of a conjoined anchor lumen may be achieved when 20-50% of one anchor overlaps the other. In some embodiments, it is determined that the structural integrity may be achieved when 30% of one anchor overlaps another. It is appreciated that the degree of overlap may vary on a case by case basis, depending upon factors such as the thickness and/or state of tissue at an anchor location. Accordingly, the present disclosure is not limited to any particular degree of anchor coil overlap for a conjoined anchor lumen.

As referred to above, one advantage of the implant disclosed herein results from the angular introduction of the anchors into the annular tissue as shown in FIGS. 5A-5D. By introducing anchors along the curve of the guidance device (or otherwise at an angle, generally towards a mating anchor pair) rather than normal to the plane of the annular surface, the depth of anchor penetration may be reduced. Being able to reduce the depth of anchor penetration in the delicate cardiac area reduces the potential for inadvertent damage. Although the depth of penetration is reduced, the strength of the anchor is not sacrificed but is rather enhanced by the bond of the paired anchors.

Figure 6A:
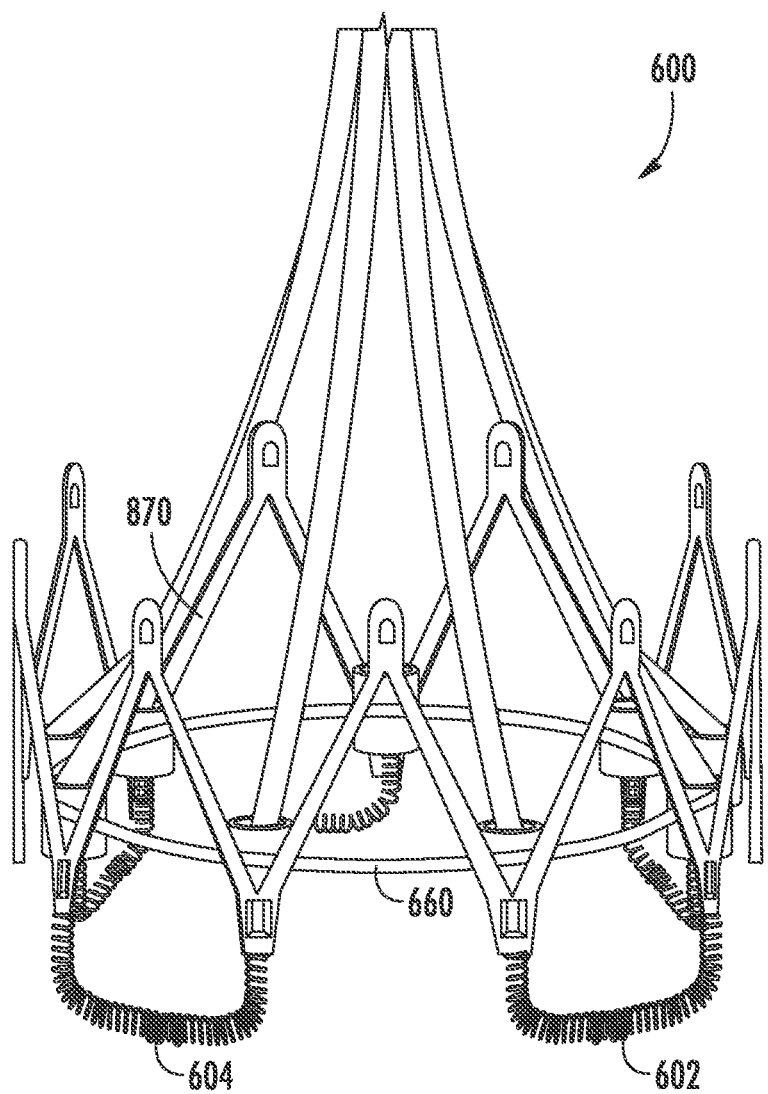
FIGS. 6A and 6B illustrate various embodiments of a frame as disclosed herein in respective expanded and cinched configurations.

In one embodiment, successive pairs of anchors may be conjoined at their distal ends around the valve annulus. Referring now to FIG. 6A, an exemplary frame 600 is shown having several constructed conjoined anchor lumens such as lumen 602 and lumen 604. In an exemplary embodiment, a frame may releasably support sixteen (16) anchors which may be conjoined to form 8 anchor lumens. Other embodiments including variants to form 2, 3, 4 and 5 conjoined anchor lumens are also envisioned. In addition, embodiments that use a combination of anchors positioned normal to the valve annulus with one or more conjoined anchor lumens are also contemplated hereby. In short, the present disclosure is not limited to any particular embedded anchor architecture.

Figure 6B:
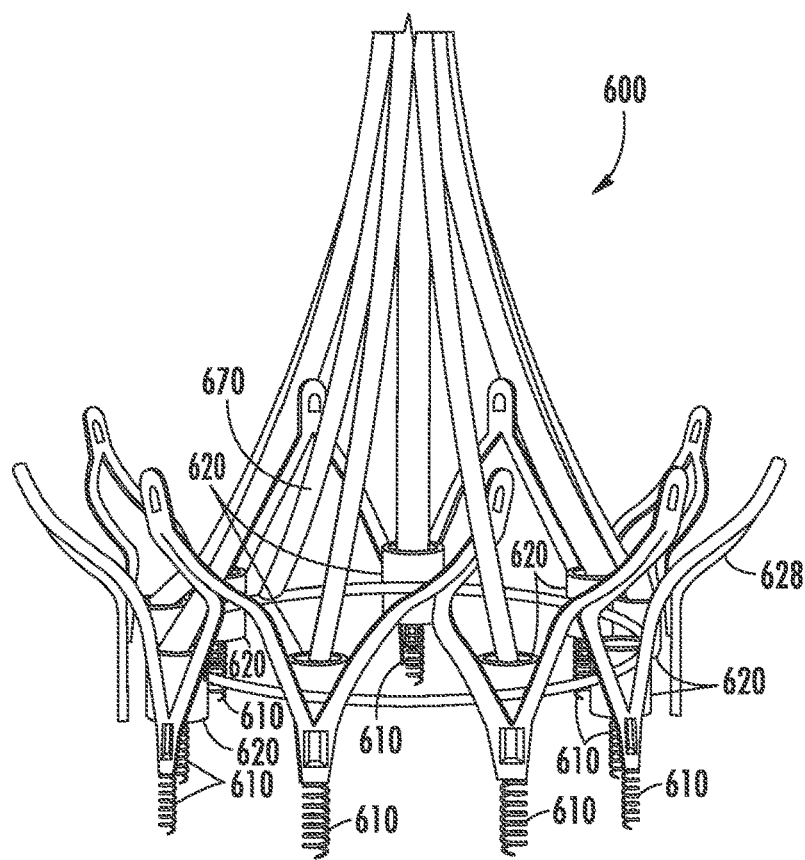

Once the conjoined anchor portion of the implant is constructed, the frame may be used to adjust the shape of the valve, for example by compressing, cinching, or otherwise decreasing the diameter of an opening defined by the frame 600. Various method of cinching the frame may be used. For example, in FIG. 6A, a lasso type cinch cord 660 is shown disposed within the frame. The cinch cord may be coupled to a cinch drive tube 870, which may be configured to reel in the cinch cord to pull the struts 628 together into a cinched configuration. Such configuration is shown in FIG. 6B. As shown in 6B, pulling the cinch cord pulls together the distal ends of frame struts 628, reducing the diameter of the distal end of the frame and bringing the anchor sleeves 620 closer together so that the anchors 610 are pulled relatively closer together. In some embodiments, the cinch drive tube 670 may be adapted to withdraw the cinch cord back into the catheter, using a hook or other device, to reduce the diameter of the frame 600.

Various other methods may be used to cinch the anchors together. For example, in some embodiments the frame may be comprised of a shape memory material which is biased towards frame compression but maintained open during conjoined anchor lumen construction using struts or other bracing devices. In such designs, compression may be achieved by removing or otherwise displacing the strut to allow compression.

Figure 7:
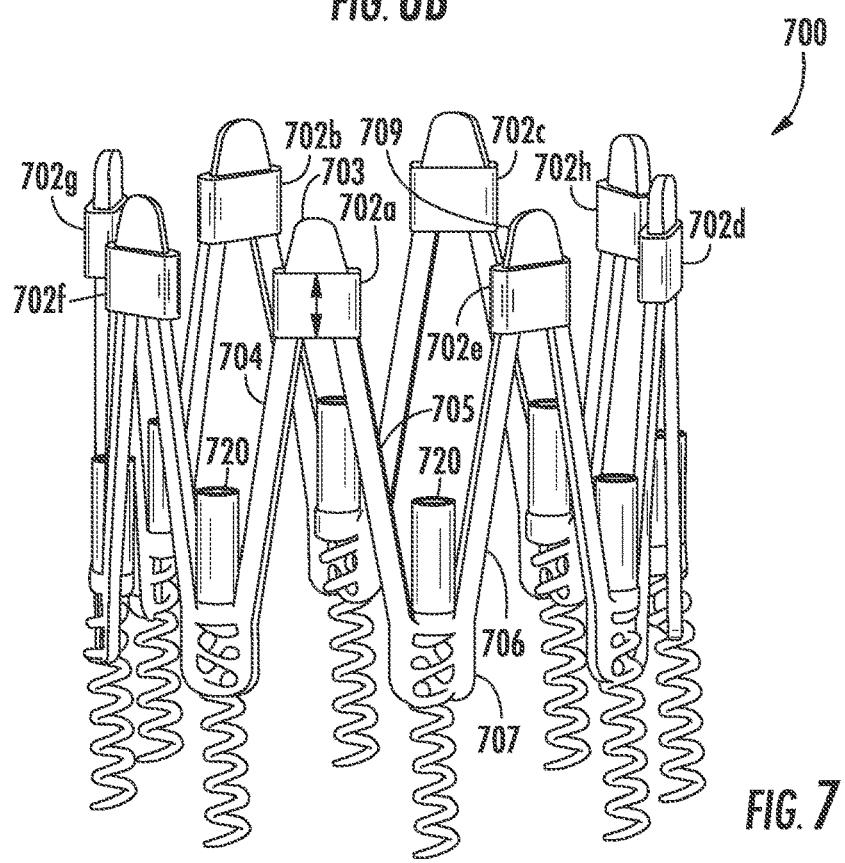
FIG. 7 illustrates an alternate embodiment of a frame cinch mechanism in accordance with an embodiment of the present disclosure.

In other embodiments, as shown in FIG. 7, moveable collars may be positioned on the upper apices of the frame struts, and frame adjustment may be achieved by driving the collars axially up and down the upper apices to expand and contract the relative distance between struts. One such method is described in U.S. patent application Ser. No. 15/352,288 filed November 2016 entitled "IMPLANTABLE DEVICE AND DELIVERY SYSTEM FOR RESHAPING A HEART VALVE ANNULUS" (hereinafter "the '288"). FIG. 7 illustrates a frame 700 that may use concepts of the '288 to provide a cinch mechanism for use in the system, device and method disclosed herein, wherein pairs of adjacent struts (704, 705, 706) meet at an apex. At least a first pair of adjacent struts (704, 705) meets at an upper apex or crown 703 at the upper portion of frame 700. At least a second pair of adjacent struts (705, 706) meets at a lower apex or crown 707 at the lower portion of the frame 700. The terms "apex," "apices," and the like may be used interchangeably with terms "crown," "crowns," and the like, as used herein and as used in any reference incorporated by reference herein, unless otherwise stated. The upper and lower crowns may be spaced sequentially along the circumference of the frame 700, with one of the upper crowns 703 followed by one of the lower crowns 707, followed by another one of the upper crowns 709, etc. In the illustrated embodiment, there are eight upper crowns and eight lower crowns, although the disclosed embodiments are not limited to any particular frame architecture.

According to one aspect, the upper crowns may be configured to have a restraint such as a collar 702a-702h fitted over and/or around the upper crown. Thus, the upper crowns may include various features, dimensions, etc. as described herein for coupling with the collars 702a-702h.

According to one embodiment, the collars 703a-703h provide a cinch mechanism to reduce the diameter of the frame and as a result, a coupled valve annulus. To 'cinch' the frame, or to otherwise bring into closer proximity one or both of the distal apices and/or proximal apices of frame 700, according to one embodiment collar 702a may be axially translated along the struts 704, 705. Distal advancement of collar 702a along struts 704, 705 urges struts 704 and 705 closer together, thereby pulling together the frame (which has been secured to valve annular tissue as described above), thereby modifying the relative positions of implanted anchors and concomitantly the shape of the valve annulus. In one embodiment, the collar 702a may be configured such that action upon the collar by a driver moves the collar along the struts 704, 705, either by pushing, rotating or other method. With such an arrangement, each collar is independently controllable to allow increased control over the relative spacing of anchors.

Various other methods of adjusting the frame to modify the shape of the annulus may be substituted herein without affecting the scope of the disclosure.

Following adjustment, the relative position of the conjoined anchors may be bound or otherwise secured by coupling the anchor heads of the conjoined anchors using cinch cord, for example such as cinch wire and/or suture material such as nylon filament or the like.

Figure 8:
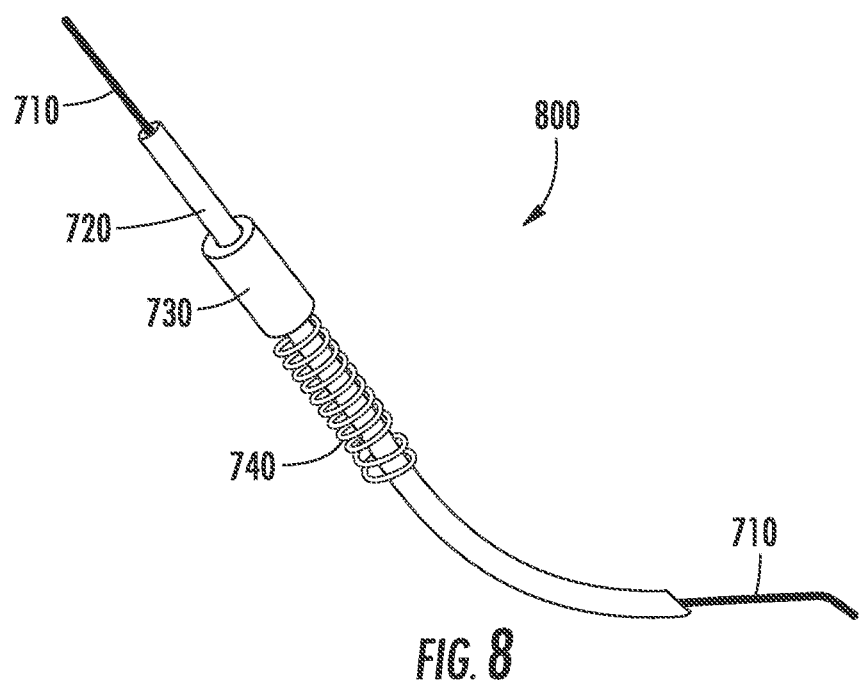
FIG. 8 is a diagram of one embodiment of a guidance device in accordance with an embodiment of the present disclosure.

According to one aspect, in one embodiment securing proximal anchor ends in a desired adjusted configuration advantageously utilizes the luminal path provided by the guidance devices/conjoined anchors to forward cinch cord to anchor head locations of the embedded implant. For example, FIG. 8 illustrates components of a frame 800 that may be translated through an anchor sleeve using methods disclosed herein. A guidance device 720 may be advanced through an anchor head 730 during deployment of an anchor 740 to the valve annulus site. Cinch cord 710 (comprising a cinch wire, suture material or coupling material) may be advanced through the luminal path of one anchor into a luminal path of the other anchor.

FIGS. 9A-9C are provided to illustrate an exemplary method for binding together anchor heads to position the implant using the luminal path created by guidance devices and anchors. In FIG. 9A, a portion of the frame 800 includes four anchor sleeves 801-804, four anchor heads 806-809 coupled to four drive tubes 811-814, and four anchors 816-819, where pairs of anchors 816, 817 and 818, 819 form respective conjoined anchor portions 810, 820. Guidance devices comprising guide tubes 826-829 may extend through the drive tubes 811-814, through anchor sleeves 801-804 and anchor heads 806-809, through anchors 816-819 and into conjoined anchor portions 810, 820 as described with regard to FIG. 9A. For each anchor pair, guide tubes may thus provide (together with the conjoined portion of the distal anchor pairs) a unitary lumen between anchor heads of the anchor pair.

According to an exemplary embodiment, anchor heads may be bound or otherwise coupled using one or more cinch cords forwarded through the unitary lumens between anchor heads and secured at anchor heads. For example, a cinch cord 870 may be extended through drive tube 814 and anchor head 809 of anchor 819, across the unitary lumen of anchor pair 818, 819, through anchor 818 and up through drive tube 813. Similarly, a cinch cord 877 may be extended through drive tube 812 and anchor head 807 of anchor 817, across the conjoined anchor portions 810 of anchor pair 816, 817 and through anchor 816 and up through drive tube 813.

According to one aspect, binding anchor heads may include advancing the cinch cord through anchor pairs (and associated conjoined anchor portions), and, following advancement of the cinch cord through the anchor heads, terminating ends of the cinch cords and removing the drive tubes to expose terminated cinch cord ends as shown in FIG. 9B. The deployment catheter may include a working lumen for accepting a working catheter configured to connect the free ends of adjoining anchor head cinch cords. In one embodiment, the cinching may occur following removal of the anchor collars from the frame to reduce interference of the cinch cord with the anchor sleeves or other features of the frame. FIG. 9B illustrates an implant following placement of two cinch cords 870, 877 and removal of the drive tubes 811-814, freeing the frame for removal.

Once the frame is removed, a working catheter may be configured to dispose a binding mechanism such as cinch clamp between ends of cinch cords 870, 877 as shown in FIG. 9C. Alternatively, the working catheter may be configured to resistance weld ends of cinch cords 870, 877.

An exemplary binding mechanism and process may involve cinching of the frame to a desired adjusted radial profile, with the surgeon coupling pairs of anchor heads at sequential radial locations around the valve annulus. In other embodiments, anchor head pairs may be secured in non-sequential and/or random order. In some embodiments, securing may occur after release of all drive tubes from anchor heads, or after release of only some of the drive tubes through the anchor heads. In some embodiments, securing may occur following removal of the frame from the valve annulus site, although it is appreciated that the frame may advantageously provide structure, support, and stability during cinch cord deployment. In some embodiments, the frame may be used to support an ICE catheter that may be used to radially view anchor head locations during securing of the cinch cords to anchor heads.

FIG. 10 illustrates a second system for binding or otherwise securing the anchor heads following implant adjustment. In the embodiment of FIG. 10 the system may include a tubular frame 910 (shown in cross section) having a spool housing 915 mounted thereon, where the spool housing may be positioned relatively proximate on the frame in a manner that reduces interference with frame expansion, anchor deployment, cinching and other frame functions. The spool housing 915 may store cinch cord 950, such as cinch wire, suture material or the like that may be used to couple the anchor heads. A working catheter 940 may be advanced within a working channel of the deployment catheter towards the anchor heads 960 and may be configured to push the cinch cord through the anchor heads. As the cinch cord is pushed through the anchor heads, additional cinch cord 950 may be spooled out, or otherwise released from, the spool housing 915. The working catheter may move between anchor heads to direct advancing cinch cord as it is spooled from the spool housing 915.

When the cinch cord has been advanced through a selected number of anchor heads (including all anchor heads or a subset of the anchor heads), the cinch cord may be cut on both ends, and the ends joined using a clamp or resistance weld as described with regard to FIGS. 9A-9C. Using a single cinch cord and thus a single clamp or weld advantageously further reduces the overall profile and potential for implant failure. In some embodiments, the use of a single cinch cord may facilitate later removal of the cord, for example if healing characteristics of the conjoined anchors (for example, tissue ingrowth, etc.) may alone stabilize the shape of the annulus.

FIGS. 11A-11E are provided to illustrate alternate binding mechanism for securing anchor heads. The system includes a working catheter 1020 that may be preloaded with anchor clips, for example anchor clips 1022, 1024 and 1026. Proximal to each proximal and distal end of each anchor clip is a flange or other feature configured for secure engagement with the anchor head. For example, anchor clips 1022, 1024, and 1026 are shown to include arms 1023, 1025 configured to engage a feature of the anchor head when inserted through the collar. In the exemplary embodiment, each arm is configured to extends away from the longitudinal axis of the clip in a direction generally normal to the clip.

FIGS. 11A-11E illustrate a representative section of an implant 1000 constructed according to the principles disclosed herein. Although it is appreciated that an annular valve is generally circular or oval in nature, the representative portion is shown linearly for ease of explanation. In addition, for purposes of explanation, only anchor heads (including anchor heads 1002, 1004, 1006, 1008, 1010, and 1012), conjoined anchor pairs 1003, 1007, and 1011 are shown.

Figure 11A:
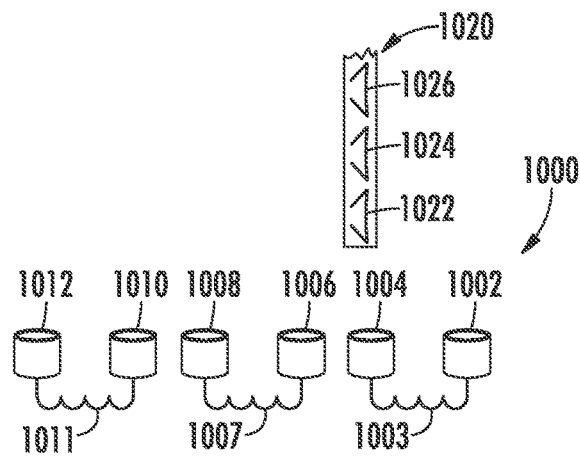
FIGS. 11A-11E illustrate a process for coupling proximate anchor ends using anchor clips in accordance with an embodiment of the present disclosure.
Figure 11B:
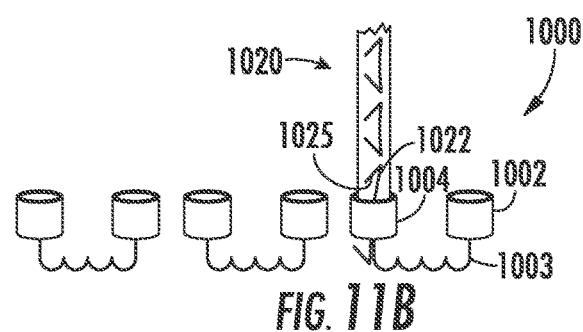

According to one aspect, once the implant 1000 is positioned and the valve annulus adjusted, for example using conjoined anchors pairs 1003, 1007, and 1011, the working catheter 1020 may be used to insert the anchor clips 1022, 1024, and 1026 into anchor heads to secure their positions relative to the reshaped annulus. FIG. 11B illustrates working catheter 1020 positioned proximate to anchor head 1004. In one embodiment, working catheter 1020 may be releasably couplable to the anchor head 1004, using a detachable hook or other means, although this is not a requirement. The working catheter 1020 may be controlled to advance a distal end of an anchor clip 1022 through the anchor head 1004 until the anchor clip arm 1023 is released from anchor head 1004. The reverse bias of anchor clip arm 1023 may engage a distal end of the anchor head 1004, securing the anchor clip 1022 within the collar. The working catheter may comprise features to preclude the proximal end of anchor clip from exiting the working catheter.

Figure 11C:
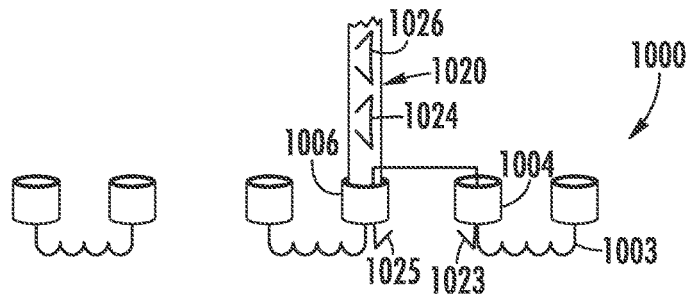

As shown in FIG. 11C, the working catheter may then be advanced to anchor head 1006, where the proximal end of anchor clip 1022 may be inserted into anchor head 1006 via manipulation by the working catheter. For example, in one embodiment, the working catheter may comprise a push rod configured to push anchor clip 1022 through anchor head 1006 until anchor clip arm 1025 extends past the distal end of the anchor head 1006, thereby freeing the arm and enabling the arm to engage with the anchor head. As a result, anchor clip 1022 secures the position of anchor heads 1004 and 1006.

Figure 11D:
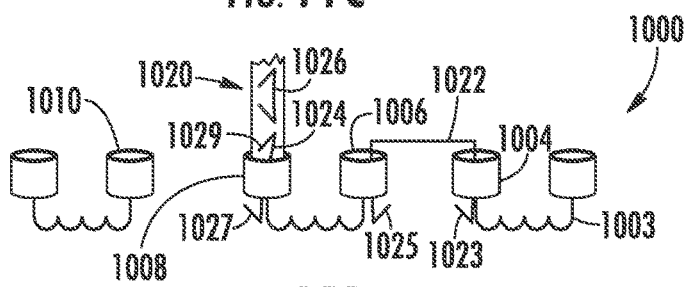
Figure 11E:
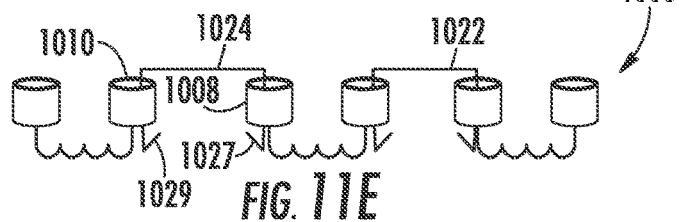
Figure 12A:
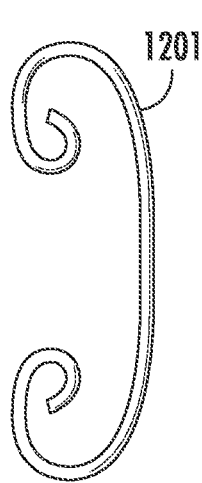
FIGS. 12A-12D illustrate various exemplary anchor clips that may be used in the process of FIGS. 11A-11E.
Figure 12B:
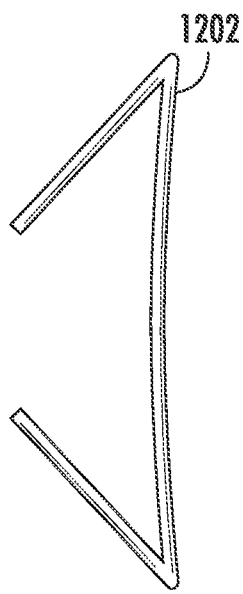
Figure 12C:
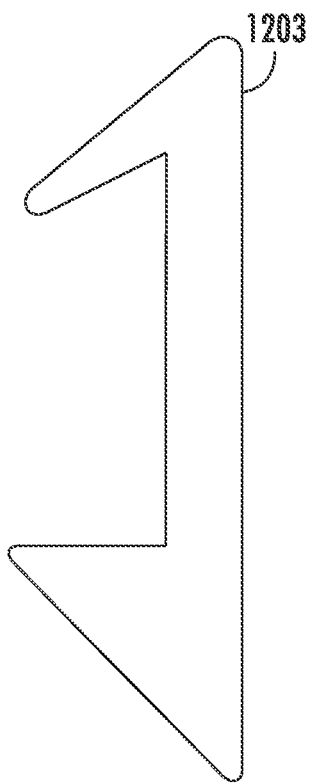
Figure 12D:
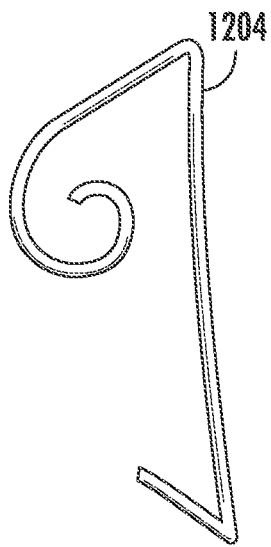

Following placement of anchor clip 1022, working catheter may be advanced to anchor heads 1008 and 1010, as shown in FIGS. 11D and 11E, to deploy anchor clip 1024 with arms 1029, 1027 extending through anchor housings, and retain or otherwise bind anchor head positioning.

FIGS. 12A-12D illustrate exemplary configurations of anchor clips 1201, 1202, 1203, and 1204. In general, the anchor clip comprises a first, compressed configuration permitting the anchor clips to slideably move through a working catheter, and a second, at least partially expanded configuration where one or more flanges or other clip features securely engage the clip to the anchor head. For example, the anchor clip may have an expanded configuration wherein at least a portion of the clip extend away from the longitudinal axis of the anchor clip to facilitate engagement with an anchor head. FIGS. 12A-12D illustrate such examples, including curves, arms, protuberances or other features that may be included the anchor clip to secure the clip to the anchor head. As shown in FIGS. 12A-12D, there may be various different mechanisms, and proximal and distal features of the anchor clip may differ. It should be understood that the illustrated embodiments are provided by way of example only, and that different configurations may be identified by those of skill in the art for engagement with various different anchor head designs. In various embodiments, anchor clips may be made of a suitable biocompatible metal alloy such as stainless steel, cobalt chromium, platinum iridium, nickel titanium, other suitable materials, or combinations thereof and/or may be coated with a drug-eluting material to prevent fibrosis and/or clotting.

Accordingly, a variety of binding mechanisms for coupling anchor heads have been shown and described, including mechanisms which utilize the conjoined anchor lumen and those that clip the anchor heads. It is appreciated that the various system and methods may be used alone or in combination and that the order of delivery to anchor heads is a matter of design.

Once the proximal and distal ends of the anchors have both been secured, the frame may be removed from an annulus deployment site. In some embodiments, release of the frame may be accomplished by releasing the drive tubes as described with regard to FIG. 9B. Various methods of releasing the drive tubes from the anchor head are envisioned. In one embodiment, as described briefly with regard to FIG. 3C, the drive tube may be configured with one or more keys or flanges that engage one or more notches (327a, 327b) of the anchor head, and release of the drive tube may be achieved by withdrawing the flanges from the notches of the anchor head. Other forms of keying or detent mechanisms may be readily substituted herein by those of skill in the art and are considered within the scope of the disclosure.

Once drive tubes are released the frame may be compressed. Compression of the frame may occur automatically, for example frames that are formed of a shape memory material that are biased towards a compressed state may naturally assume the compressed state as the drive tubes are released from the anchor heads. Alternatively, frame designs that include mechanical methods for compressing the frame may be used. Such designs include but are not limited to frames including slideable collars surrounding proximal strut apices that may be advanced distally to draw the struts together and compress the frame such as described with regard to FIG. 7. The compressed frame may be withdrawn back into the deployment catheter for removal from the patient, leaving only the anchor heads, cinch cord and conjoined anchor pairs in place.

Figure 13:
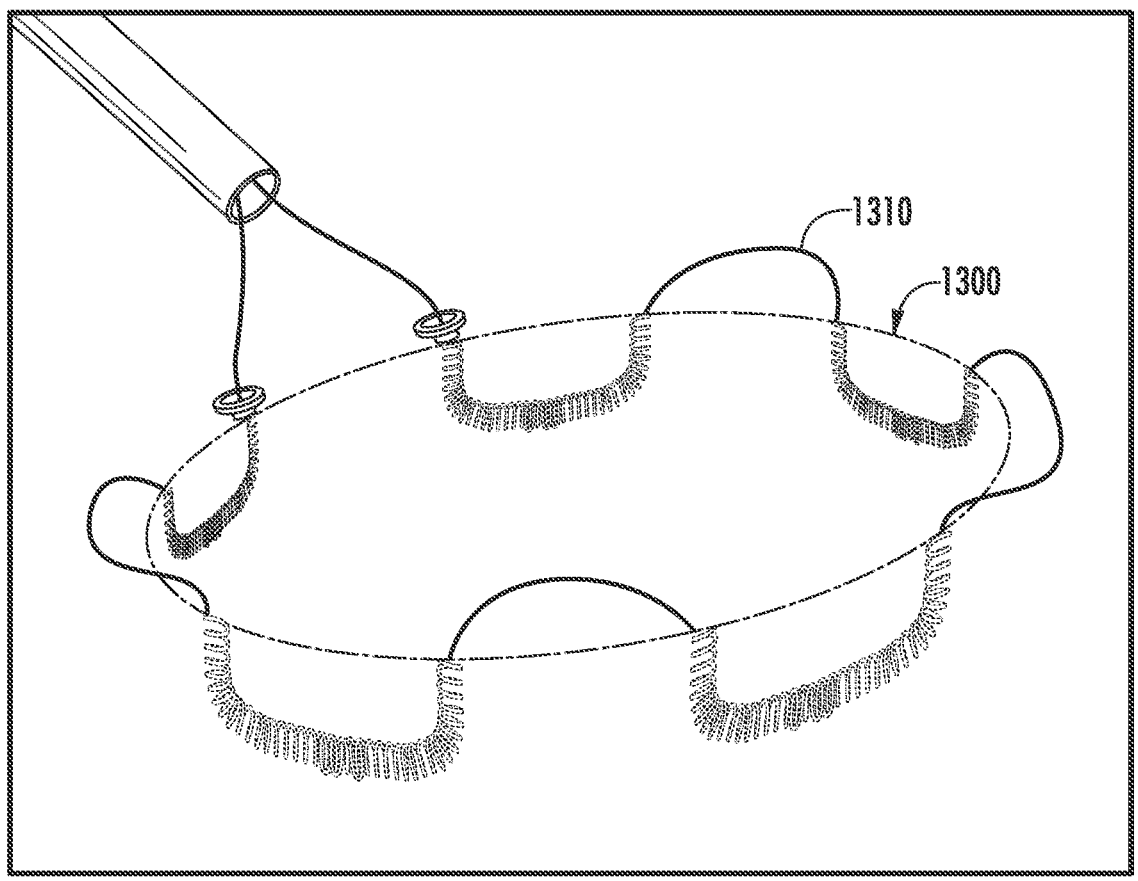
FIG. 13 illustrates an implant constructed as disclosed herein following frame removal in accordance with an embodiment of the present disclosure.

FIG. 13 illustrates a perspective view of a valve annulus (indicated generally by dashed line 1300) showing a portion of a conjoined anchor implant 1310 constructed according to principals disclosed herein following removal of the frame. As shown in FIG. 13, only a small portion of the implant is above the tissue line of the atrium, with the remainder of the implant embedded within patient tissue. The low-profile of the conjoined anchor implant 1310 minimizes implant bulk and the related potential for implant fracture and/or contact between the heart tissue and the implant, thereby reducing embolic and thrombus risk. Angularly embedded and conjoined anchors provide structural integrity and improved implant retention while moving more flexibly with the patient's anatomy to reduce trauma over time.

Figure 14:
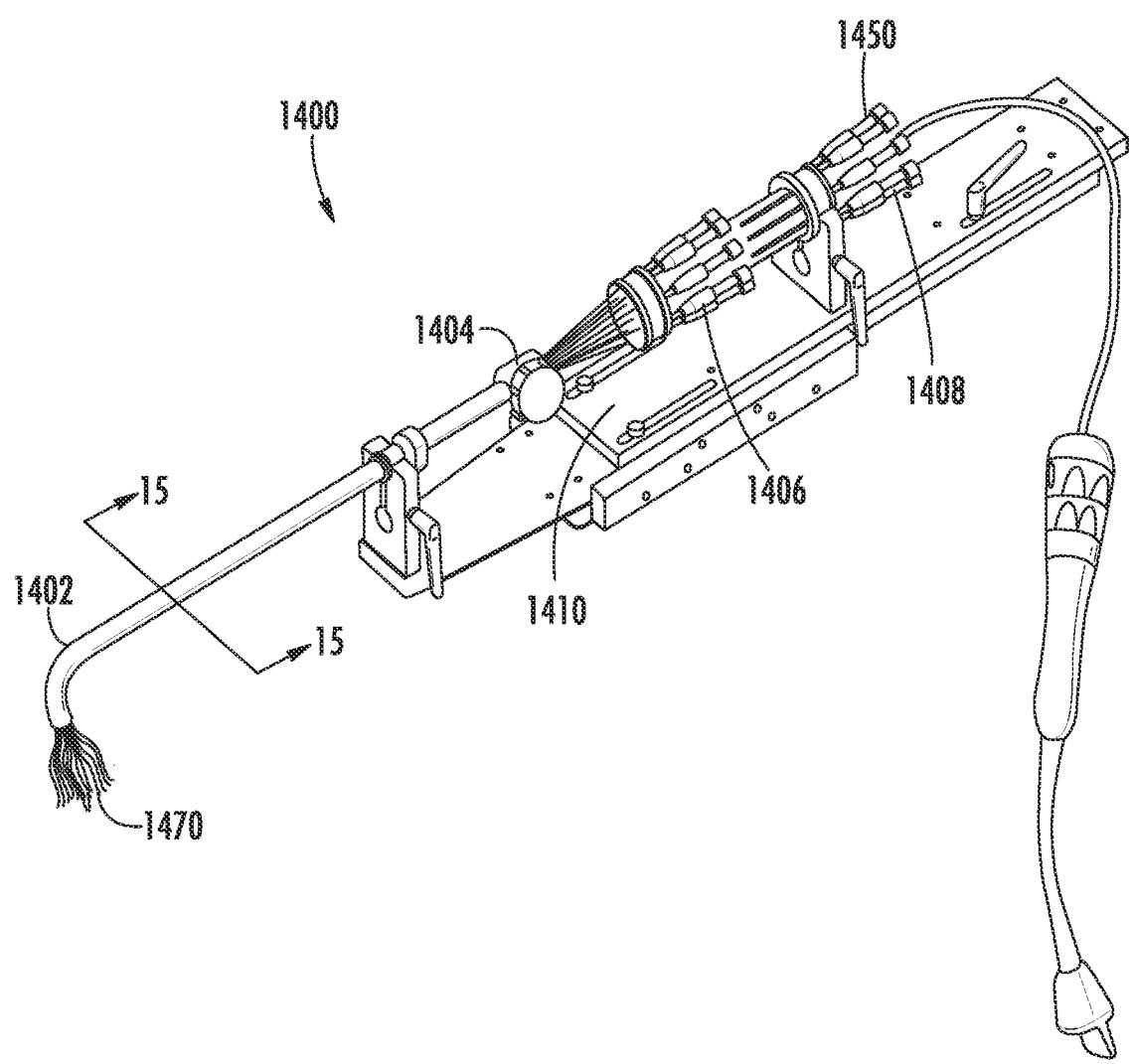
FIG. 14 illustrates one embodiment of a deployment catheter that may be used in accordance with various embodiments of the present disclosure.

FIG. 14 is a perspective view of an exemplary deployment system 1400 that may be used for annular reshaping as described herein. The deployment system 1400 comprises a steerable sheath 1402, a sheath steering knob 1404, cinch knobs 1406, anchor knobs 1408, implant deployment components that may be used to construct the conjoined anchor implant described herein, an ICE probe 1470, all supported and secured to a base 1410. The cinch knobs 1406 and anchor knobs 1408 may be spring loaded to maintain tension. Rotation of the anchor knobs 1408 may rotationally advance the helically wound anchors 1420 into conjoined anchor pairs within the annular tissue such that conjoined anchor pairs surround or partially surround a valve annulus. Cinch knobs 1406 may be manipulated by an operator to compress an expandable frame, coupled to the anchors, to reduce a valve annulus. Cinching/Suture knobs 1450 may control access to and/or capabilities of a working catheter configured to secure proximate ends of anchors in fixed position to maintain the reduced valve annulus as described herein. Anchor knobs 1408 may be further controlled to release the expandable frame, leaving the implant in its secured position.

Figure 15:
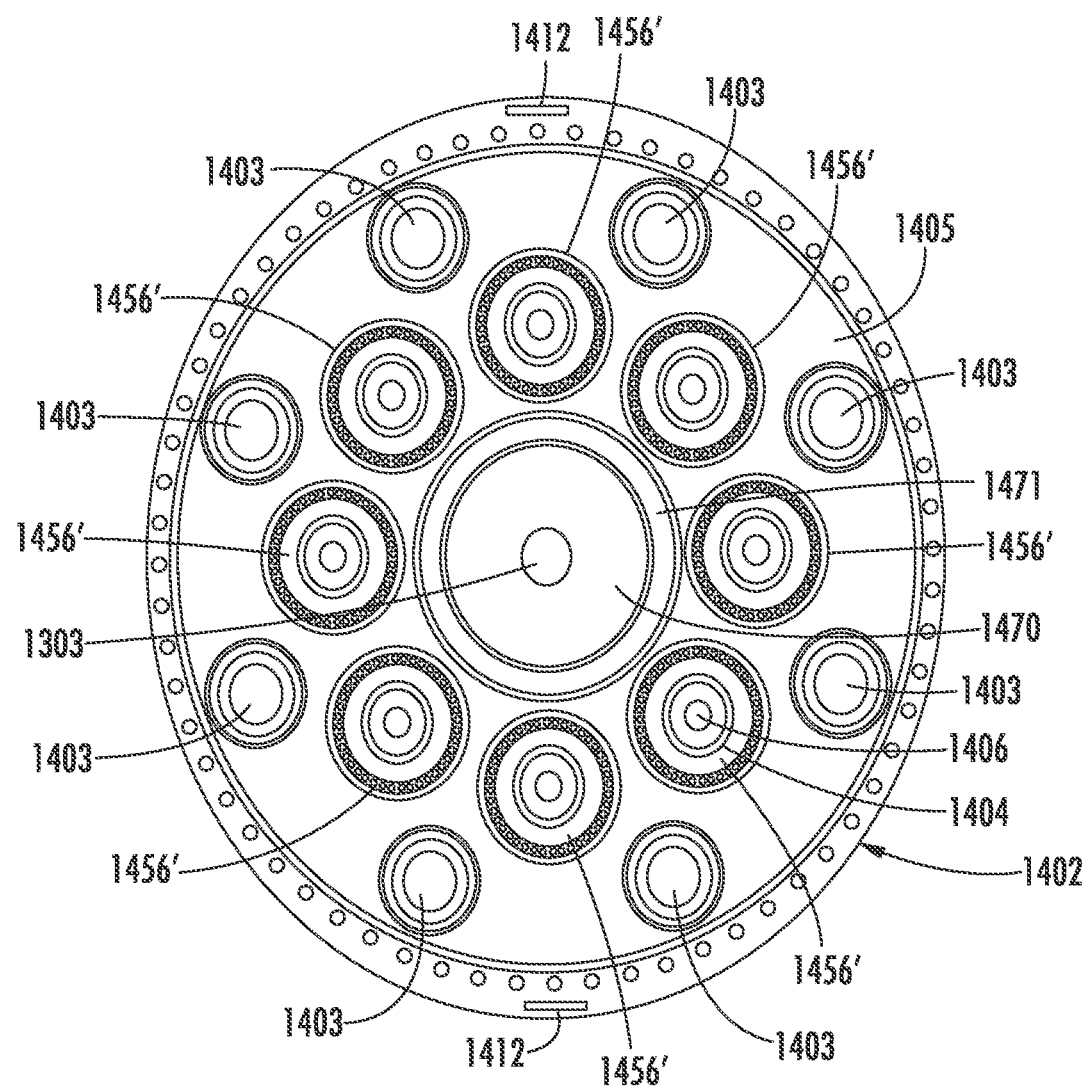
FIG. 15 is a cross section of the deployment catheter of FIG. 13.

FIG. 15 is a cross section taken along line 15-15 of FIG. 14. The pull wires 1412 may be attached to the sheath steering knob 1404 to deflect the distal end of the sheath 1402. The sheath 1402 may be a steerable outer sheath 1402, for example made of braided polymer or metal such as Nitinol or stainless steel. An ICE catheter shaft 1470 may be centrally located with the guidewire lumen 1303 located within the ICE catheter lumen 1471, wherein the implant frame may be deployed through the ICE catheter lumen 1471 for positioning proximate to the valve annulus, prior to insertion of the ICE catheter. In some embodiments there may be eight anchor driver wires 1403, for example nitinol, circumferentially located within the sheath 1402. The anchor driver wires 1403 are located within anchor driver sheaths, for example laser cut hypotubes. As described above, anchor driver sheaths may comprise a working channel through which a guidance device may be inserted for directing anchor placement. In one embodiment there may be eight pusher tubes 1456', which may be braided, located around the ICE catheter shaft 1470. The pusher tubes 1456' may include a cinch retaining tube, for example a laser cut hypotube and a cinch retaining wire, for example nitinol.

Accordingly, a system and method for reshaping a valve annulus using a removable frame to construct an implant having conjoining anchors has been shown and described. The devices and/or methods disclosed and claimed herein can be made and executed without undue experimentation in light of the present disclosure. While various embodiments of the devices and methods of this disclosure have been described, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope, and concept of the disclosure as defined by the appended claims.

What is claimed is:

1. A system comprising:
   a catheter comprising a plurality of lumens extending from a proximal end of the catheter to a distal end of the catheter;
   a frame having a compressed configuration enabling translational advancement of the frame through the catheter, the frame comprising a first configuration enabling positioning of the frame at least partially around a valve annulus;
   at least one cinch mechanism coupled to the frame and configured to transition the frame between the first configuration and a second configuration different from the first configuration;
   a plurality of anchors supported by the frame, each anchor comprising a proximal end comprising an anchor head and a distal end configured for mated engagement with another anchor of the plurality of anchors to form a conjoined anchor pair, each anchor comprising an anchor lumen extending from a proximate anchor end to a distal anchor end; and a guidance device axially translatable within the anchor lumen and through tissue of the valve annulus, the guidance device configured to define a path through tissue of the valve annulus from a first anchor towards a second anchor, the first anchor translatable over the guidance device along the path through the tissue of the valve annulus towards the second anchor to form a conjoined anchor pair.

2. The system of claim 1, wherein the first configuration comprises a tissue engaging configuration and the second configuration comprises an annulus reshaping configuration, and wherein the first configuration is larger than the second configuration.

3. The system of claim 2, further comprising a binding mechanism to secure the plurality of anchors in positions associated with the annulus reshaping configuration to retain the annulus reshaping configuration.

4. The system of claim 3, wherein the binding mechanism comprises one or more of a cinch wire, a suture wire or an anchor clip and one or more of a cinch clamp or a resistance weld band.

5. The system of claim 4, further comprising a plurality of drive tubes, each drive tube disposed within one of the plurality of lumens of the catheter, one drive tube coupled to each anchor, wherein each drive tube is configured to advance an associated anchor over the guidance device.

6. The system of claim 5, wherein the guidance device is configured for axial translation through a drive tube lumen of a drive tube into the anchor lumen.

7. The system of claim 6, wherein the guidance device comprises a curved distal end configured to direct the anchor away from a plane normal to the valve annulus.

8. The system of claim 7, wherein the drive tube is configured to translate the distal anchor end past the curved distal end of the guidance device.

9. The system of claim 8, wherein the guidance device comprises at least one of a guide-wire or a guide tube.

10. The system of claim 9, wherein the guidance device comprises a guide tube and wherein the binding mechanism couples paired anchor heads through a lumen of the conjoined anchor pair.

11. The system of claim 1, wherein the frame comprises a plurality of anchor sleeves corresponding in number to the plurality of anchors, each anchor sleeve configured to releasably support an associated anchor for deployment of the associated anchor at least partially around a valve annulus.

12. The system of claim 1, wherein the cinch mechanism comprises a cinch wire surrounding one of an internal or external radius of the frame, and a drive tube configured to withdraw the cinch wire to reduce an internal volume of the frame.

13. The system of claim 1, wherein the frame comprises a plurality of upper crowns, each upper crown comprising a pair of struts having a space therebetween, and the cinching mechanism comprises a plurality of collars, each collar at least partially surrounding each upper crown and configured to translate axially relative to the frame to adjust the space between the pair of struts of an associated upper crown.

14. The system of claim 1, wherein the plurality of anchors comprises a plurality of helical coils, and wherein the conjoined anchor pair comprises a plurality of overlapping coils of a helical coil pair.

15. An implant comprising:
a plurality of anchors, each anchor comprising a distal end sharpened for advancement through tissue of a valve annulus towards another of the plurality of anchors, each anchor configured for mating engagement with the another of the plurality of anchors when embedded in the tissue of the valve annulus to form a conjoined anchor pair; and
a binding mechanism, coupling proximal ends of at least two anchors, to retain the at least two anchors in a predetermined configuration.

16. The implant of claim 15, wherein the predetermined configuration is a valve annulus reshaping configuration and the binding mechanism comprises one or more of a cord, a wire, a filament and a clip.

17. The implant of claim 16, wherein each anchor comprises a proximal end comprising an anchor head and wherein the binding mechanism couples together at least some of the anchor heads of the plurality of anchors.

18. The implant of claim 17, wherein the conjoined anchor pair comprises an anchor lumen extending at least partially therethrough and wherein the binding mechanism couples a pair of anchor heads using a path including the anchor lumen.

19. A method for reshaping a valve annulus includes the steps of:
deploying an expandable frame releasably supporting a plurality of anchors through a delivery catheter to a valve annulus repair site;
driving at least two of the plurality of anchors into tissue around the valve annulus including matingly engaging distal tips of anchors to form anchor pair at least partially around the valve annulus;
compressing the expandable frame to reshape the valve annulus to an annular reshaping configuration;
binding proximal ends of anchor pairs;
releasing the plurality of anchors from the expandable frame; and
removing at least a portion of the expandable frame from the valve annulus repair site.

20. The method of claim 19, wherein the step of driving the plurality of anchors into tissue around the valve annulus includes the steps of, for each pair of anchors of the plurality of anchors:
selecting an anchor including identifying a paired anchor;
inserting a guidance device through a first lumen extending from a proximal end of the delivery catheter through a distal anchor tip of the selected anchor, wherein the guidance device comprises a curve at a distal tip configured to guide the selected anchor to the paired anchor and wherein inserting the guidance device through the distal anchor tip of the selected anchor cuts a first path through tissue towards the paired anchor;
advancing the selected anchor over the guidance device towards the anchor pair;
inserting a guidance device through a second lumen extending from a proximal end of the catheter through a distal anchor tip of the paired anchor, wherein the curve at a distal tip of the guidance device cuts a path through tissue towards the selected anchor;
advancing one or both of the selected anchor and the paired anchor towards each other to conjoin distal ends of the selected anchor and the paired anchor.

* * * * *